US012019128B2

(12) United States Patent
Srinivasan

(10) Patent No.: US 12,019,128 B2
(45) Date of Patent: Jun. 25, 2024

(54) ACCESSIBLE MAGNETIC RESONANCE IMAGING SYSTEM

(71) Applicant: Advanced Imaging Research, Inc., Cleveland, OH (US)

(72) Inventor: Ravi Srinivasan, Beachwood, OH (US)

(73) Assignee: ADVANCED IMAGING RESEARCH, INC., Cleveland, OH (US)

( * ) Notice: Subject to any disclaimer, the term of this patent is extended or adjusted under 35 U.S.C. 154(b) by 305 days.

(21) Appl. No.: 17/774,518

(22) PCT Filed: Nov. 4, 2020

(86) PCT No.: PCT/US2020/058771
§ 371 (c)(1),
(2) Date: May 5, 2022

(87) PCT Pub. No.: WO2021/091931
PCT Pub. Date: May 14, 2021

(65) Prior Publication Data
US 2022/0381859 A1 Dec. 1, 2022

Related U.S. Application Data

(60) Provisional application No. 62/931,379, filed on Nov. 6, 2019.

(51) Int. Cl.
*G01R 33/3815* (2006.01)
*G01R 33/38* (2006.01)
(Continued)

(52) U.S. Cl.
CPC ..... *G01R 33/3815* (2013.01); *G01R 33/3804* (2013.01); *G01R 33/3856* (2013.01);
(Continued)

(58) Field of Classification Search
CPC ............ G01R 33/3804; G01R 33/3815; G01R 33/3856; G01R 33/421; G01R 33/422; G01R 33/5634; G01R 33/58
See application file for complete search history.

(56) References Cited

U.S. PATENT DOCUMENTS 4,612,505 A    9/1986  Zijlstra
5,659,281 A    8/1997  Pissanetzky et al.
(Continued)

FOREIGN PATENT DOCUMENTS

EP    1 447 858 B1    8/2008

OTHER PUBLICATIONS

International Search Report and Written Opinion from corresponding International Patent Application No. PCT/US2020/058771, dated May 11, 2021.
(Continued)

*Primary Examiner* — Gregory H Curran
(74) *Attorney, Agent, or Firm* — KUSNER & JAFFE

(57) ABSTRACT

An ambulance-compatible magnetic resonance imaging (MRI) system for on-site emergency diagnosis includes a mid-field super-conducting head-only magnet including a bore and an active shield arranged relative to the magnet, a passive shield arranged relative to the magnet, the passive shield including a first flange arranged adjacent to a first side of the magnet bore, a second flange arranged adjacent to a second side of the magnet bore, wherein the first flange and the second flange are electrically connected to each other, and wherein the passive shield is operative to capture flux extending out from the magnet bore and return the flux to the magnet. An asymmetric head gradient assembly for generating magnetic gradient field in the mid-field super-conducting magnet is also provided, the magnetic gradient field being between 100-150 mT/m or having a slew rate between
(Continued)

400-800 T/m/s. The MRI system includes a receiver coil and a controller operatively coupled to the receive coil, the controller configured to produce an image based on data obtained from the receive coil. The MRI system is mountable in an ambulance vehicle.

13 Claims, 7 Drawing Sheets

(51) Int. Cl.
G01R 33/385 (2006.01)
G01R 33/421 (2006.01)
G01R 33/422 (2006.01)
G01R 33/563 (2006.01)
G01R 33/58 (2006.01)

(52) U.S. Cl.
CPC ......... *G01R 33/421* (2013.01); *G01R 33/422* (2013.01); *G01R 33/56341* (2013.01); *G01R 33/58* (2013.01)

(56) References Cited

U.S. PATENT DOCUMENTS

| | | | | |
|---|---|---|---|---|
| 6,817,866 B1* | 11/2004 | Ginzburg | ............... | G09B 25/00 434/365 |
| 7,954,882 B2* | 6/2011 | Brummel | ................. | B60P 3/14 296/181.6 |
| 11,432,976 B2* | 9/2022 | Baer | .................... | A61G 3/0833 |
| 2016/0310229 A1 | 10/2016 | Bammer et al. | | |
| 2017/0143271 A1 | 5/2017 | Gustafsson et al. | | |

OTHER PUBLICATIONS

Pierpaoli, P. et al., "Polyvinylpyrrolidone (PVP) water solutions as isotropic phantoms for diffusion MRI studies", International Society for Magnetic Resonance in Medicine, 1414 (Jan. 1, 2009).

Hartwig, A. et al., "2D Nose Navigators (NoseNav) for real-time correction of nodding motion in brain MRI", International Society for Magnetic Resonance in Medicine, ISMRM, 2030 Addison Street, 7th Floor, Berkeley, CA 94704 USA, 3757 (Apr. 7, 2013).

Wilm, Bertram J. et al., "Diffusion MRI with Concurrent Magnetic Field Monitoring", Magnetic Resonance in Medicine, vol. 74, No. 4 (Jul. 17, 2015).

Lee, Seung-Kyun et al., "Peripheral Nerve Stimulation Characteristics of an Asymmetric Head-Only Gradient Coil Compatible with a High-Channel-Count Receiver Array", Magnetic Resonance in Medicine, vol. 76, No. 6 (Dec. 2, 2015).

Panther, Alex et al., "A Dedicated Head-Only MRI Scanner for Point-of-Care Imaging", International Society for Magnetic Resonance in Medicine, ISMRM, 2030 Addison Street, 7th Floor, Berkeley, CA 94704 USA, No. 3679 (Apr. 26, 2019).

Stainsby, Jeff A. et al., "Imaging at 0.5 T with high-performance system components", International Society for Magnetic Resonance in Medicine, ISMRM, 2030 Addison Street, 7th Floor, Berkeley, CA 94704 USA, No. 1194 (Apr. 26, 2019).

Wald, Lawrence L. et al., "Low-Cost and Portable MRI", Journal of Magnetic Resonance Imaging, vol. 52, No. 3 (Oct. 12, 2019).

* cited by examiner

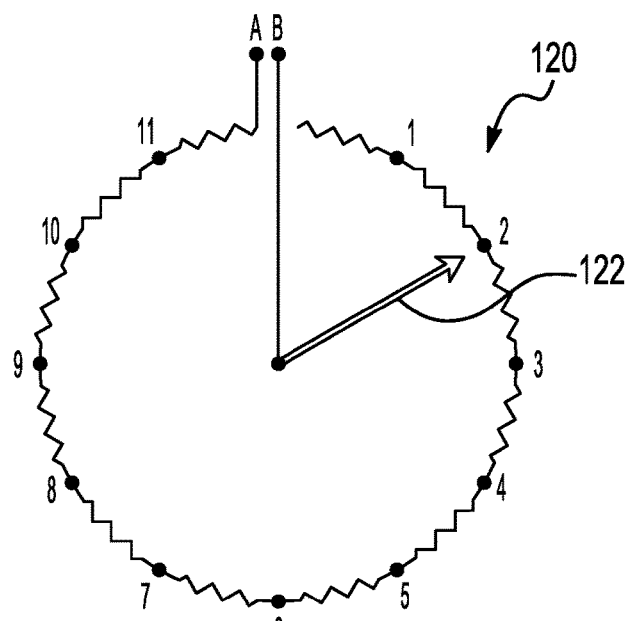
FIG. 7B
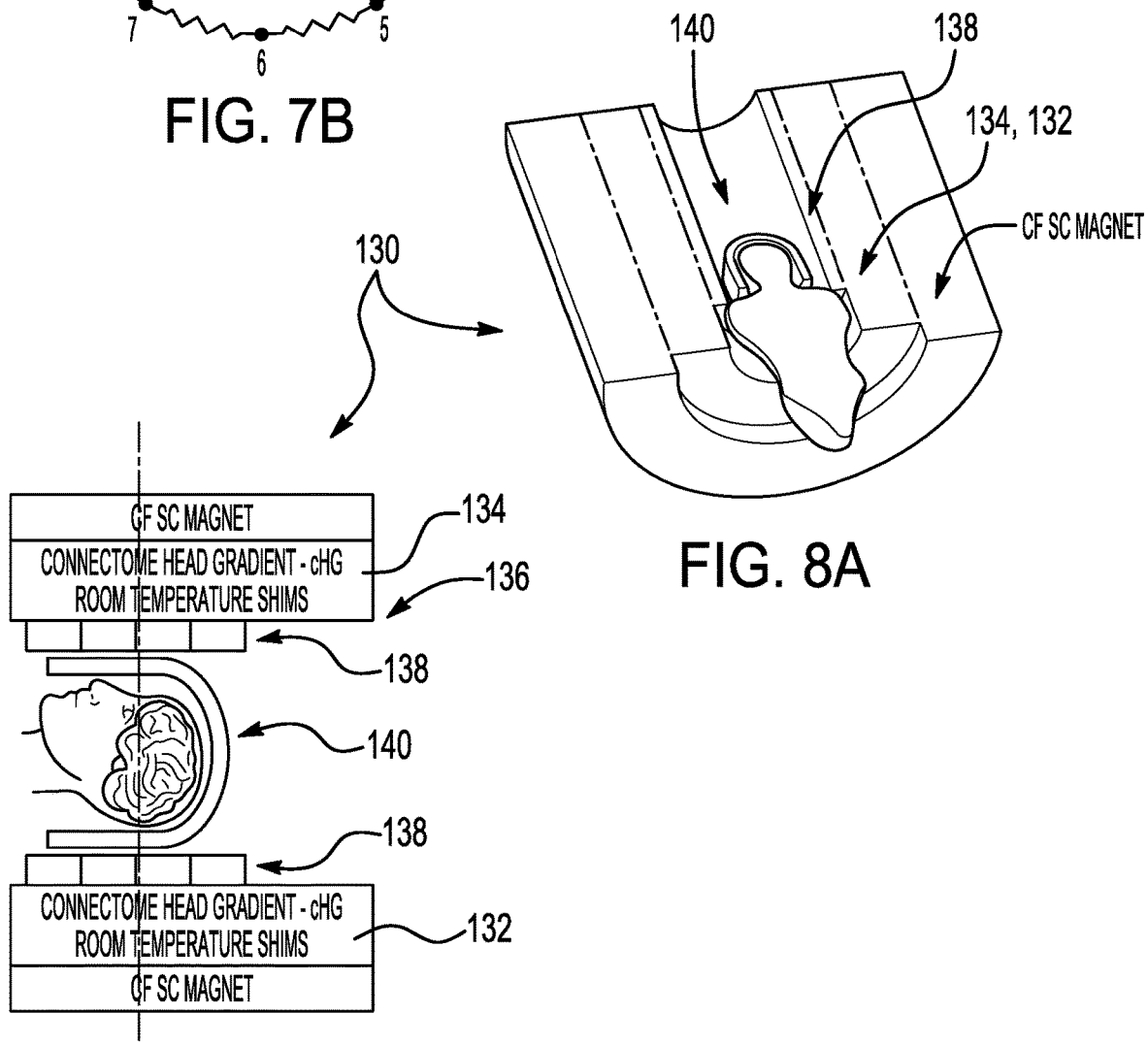
FIG. 8A
FIG. 8B

ACCESSIBLE MAGNETIC RESONANCE IMAGING SYSTEM

TECHNICAL FIELD

The present invention relates to an accessible magnetic resonance system, and to advances in magnetic resonance imaging systems, including components, installation and transport technology. More particularly, the present invention relates to an integrated diagnostic emergency ambulance centered on a magnetic resonance system.

BACKGROUND ART

Since 2010 stroke is the second leading cause of death worldwide, accounting for more than 11% of total mortality. In the United States, stroke is the fifth cause of death and a major cause for long-term disability. Stroke treatment depends on a narrow therapeutic time window, as human nerve tissue is rapidly and irreversibly lost over time.

Two forms of acute brain stroke are possible in patients, namely, ischemic and hemorrhagic. Generally, ischemic strokes are caused by blood clots blocking blood-flow, whereas hemorrhagic strokes are caused by bleeding artery, both are deleterious to health.

Early identification of acute ischemic stroke is vital in order to provide timely treatment through thrombolysis, which can improve clinical outcome and reduce resulting complications. The only systemic, acute treatment for stroke that has been proven effective is recombinant tissue plasminogen activator (r-tPA), but its recommended window of use is within 3-4.5 h from stroke symptom onset. The efficacy of intra-venous (IV) thrombolysis is a function of time, the earlier a patient is treated, the greater the likelihood he or she will have a good recovery. Despite this knowledge, patients often arrive at a hospital too late to receive maximum benefit to medical treatment. In fact, less than 5% of stroke patients are treated by thrombolysis, even in specialized stroke centers. Thrombolysis for ischemic stroke can only be performed after the possibility of a hemorrhage has been excluded by diagnosis, such as computed tomography (CT) or magnetic resonance imaging (MRI). However, irrespective of the stroke type, not all hospitals can provide timely diagnosis and time is lost transferring these patients to centers with diagnostic capability. The phrase "time is brain" (in Time is Brain—Quantified, By Jeffrey L. Saver, published in Stroke 2006; 37:263-266) emphasizes that human nervous tissue is rapidly and irretrievably lost as stroke progresses and that therapeutic interventions should be emergently pursued. Stroke victims lose two million brain cells every minute, since they die for lack of oxygen in the blood-flow, which must be corrected immediately.

Despite clear guidelines published in 2013 and 2018 (Stroke 2015, vol. 46:3024-3039, 2018, Vol. 49:e46-e110) from the American Heart Association (AHA)/American Stroke Association (ASA), early management of acute ischemic stroke patients using endovascular treatment or else by healthcare personnel is not possible, since many patients still fail to present within the narrow time window to receive maximum treatment benefit from advanced stroke therapies. For these reasons, the AHA/ASA also mentioned that acute stroke patients cannot tolerate any delays in treatment, and imaging may be far from the stroke triage or tied up with outpatient imaging.

The convergence of emergency medical services (EMS), telemedicine, and mobile technology, including the recent transportable CT scanners, has presented a unique opportunity to advance stroke care in the pre-hospital field by using a mobile stroke unit (MSU) to circumvent delay to hyperacute stroke treatment. A quick CT scan with eight, 10 mm slices over the brain including an angiographic CT study to evaluate blood flow takes between six-seven minutes, with a portable CT scanner (for example, using a portable CT scanner, model Ceretom, from Neurological, now Samsung). This important CT scan assists to visualize and differentiate the stroke between hemorrhagic and ischemic, thereby prompting emergency treatment post diagnosis in the MSU.

With CT there always is concern of exposure to ionizing radiation (both the subject and support personnel), which is proven to cause or accelerate cancer. In addition, the brain tissue condition is not known with CT, since, unlike MRI, it cannot perform soft tissue diagnosis.

MRI, a dominant and preferred imaging modality, uses non-ionizing radiation and can deliver morphological, functional, angiographic (blood-flow), water diffusion, tissue perfusion, biochemical and tissue health information. MRI, however, is not accessible to roughly 90% of the world population, providing no room for stat diagnosis and follow-up clinical intervention, which is very unfortunate. Transport of an integrated emergency ambulance-based MRI operation outside of a hospital setting and where the electric power is unreliable or where the electric grid is neither accessible nor available does not exist at present. Installation of an MRI scanner in an ambulance is not straight forward. In some instances, immediate diagnosis is necessary in nearby residential, industrial and commercial areas, and remote areas distant from the metropolitan cities to prompt or initiate emergency medical services based clinical intervention. Likewise, the same is true for refugees away from home and soldiers on a mission.

Faster, ionizing radiation-free EMS based MSU MRI scans in six-seven minutes are very competitive with CT screening. To date, no integrated highly mobile emergency ambulance MRI system exists. In addition, replacing the CT with an MRI scanner is not straight-forward, since MRI specific Installation, Operation, Safety and Performance criteria must be satisfied.

In addition, traditional emergency ambulances are not designed to carry, operate or transport an MRI system. Larger, heavier (e.g., 53' long) commercial trucks cannot transport MRI systems to remote locations or function where the electrical grid cannot support their operation or is unavailable. But care must be provided to moderately and seriously ill patients who require on-the-spot (i.e., stat) diagnosis. For these reasons, it is beneficial to have a compact accessible MRI system outside of the hospital complex that can be transported to and operate in commercial, industrial, residential and remote (e.g., non-metropolitan) areas.

An emergency ambulance-based MRI system with interventional care does not exist at present. However introduction of ultra-low field (0.1T or less field strength) based on the Halbach permanent magnet design hand or cart portable MRI scanners, some capable of operating on 120 VAC/230 VAC outlets are described by Vidarsson (CA2967956A1, CA2884097A1), Wald (JP2018038844A), Mezrich (US2015285882A1), Rothberg (TW201811264A), McNulty (US20190250228A1), Poole (US20190257903A1), Cohen (WO2008008447A2), Sakellariou (U.S. Pat. No. 8,860,539) and Laskaris (U.S. Pat. No. 7,023,309) et al. Since signal-to-noise-ratio (SNR) of an MRI system is directly proportional to the main magnet field strength, these MRI scanners exhibit very low SNR and therefore are unsuitable for diagnostic brain MRI screening in a short time frame (e.g., six minutes). Much of the magnetic field homogeneity over the imaging FOV are in the order of 100 ppm (parts per million) or more, rendering these magnets unfit for routine clinical use. Quick de-ramping to avoid adverse events or enhance safety is not possible with a permanent magnet.

Whole-body MRI system transported in a large shipping container for quick installation (U.S. Pat. No. 7,733,089 B2 to Hobbs) and MRI use with the container as a shield (CN106716166A to Parkinson) are known. Parkinson utilized a cryogen-free high temperature superconductor magnet, whereas Hobbs utilized a traditional helium filled superconducting horizontal bore superconducting magnet. Both magnets are unrealistic for ambulance installation due to safety, size, weight and power restrictions. Parkinson although overcomes the helium component used in Hobbs' superconducting magnets and proposed using expensive high-temperature superconducting materials, but fails to overcome the impractical transport or installation of a large shipping container to remote areas and powered by means other than an available electrical grid.

WO 2014/188426 A1 to Rapoport utilizes an incubator, MRI combination and specifically discloses a conventional MRI and an isolette system that docks to the MRI scanner. Only a single channel, solenoidal transmit-receive head coil is presented given a space-limited opening for the MRI incubator. The large 1T magnet system weighs approximately 6 tons. Discussions of reducing magnet weight, quick de-ramping for enhanced safety and transport are not possible with this design. Use of inefficient RF coil and conventional incubator designs detract from the current integrated diagnostic emergency ambulance system intervention application.

SUMMARY OF INVENTION

For the abovementioned and other reasons, there is an unmet need for on-site emergency diagnosis, which is essential to precisely delineate the onset of brain injury, to determine its pathway, onset of illness, response to therapy, minimally invasive surgery planning, etc. The need for a compact, shielded, high magnet field strength necessary to provide high MRI SNR and safely installable with a 5 gauss (G) magnetic field to lie within a modified emergency ambulance with custom shielding, restraining and suspension mechanisms; use of DWI recommended for stroke imaging with strong connectome gradients, use of high SNR imaging devices essential for diagnostic image quality, simple patient docking system for quick patient positioning, one-button-push imaging protocol for ease of operation by emergency or nursing staff and automated analysis is now apparent in support of early diagnosis or diagnostic screening leading to early clinician intervention in patients seeking emergency care.

Described herein is a compact MRI system that is highly mobile and can easily be moved to various locations, without the need for connection to a power source. Specifically, an ambulance-compatible MRI system preferably includes one or more of a mid-field shielded super-conducting magnet, DWI compatible high-performance gradients, advanced RF head coil and receiver designs with quick trolley latching, one-step registration, one-step positioning alignment, single touch MR acquisition and post-processing, the system usable by untrained MR personnel.

In accordance with an aspect of the invention, an off-grid, hybrid 100 kWh battery-powered, mobile stroke brain MRI system is provided. The system can include a compact, lightweight, fast-charge magnet that can be brought to field in five minutes and turned OFF instantaneously to conserve power or avoid safety-related MR incidents. This is in contrast to conventional MRI systems that are always on, either at full power when in use or standby mode, or at half power (e.g., sleep mode, which may be implemented during night time when the system is not in use). Further, a 400A, 400V gradient power amplifier (GPA) with direct DC drive to reach maximum gradient performances (101 mT/m $G_{max}$, 450 T/m/s slew rate) is utilized. Since conversion from AC to DC does not occur, there is minimal power-factor conversion loss. The system can further include a mid-field MRI receive coil array that is super-cooled to cryogenic temperatures, and formed from high permittivity material. The system also can include external field perturbation nulling and internal patient motion correction mechanisms to improve image quality.

Also described herein is a means to install a brain MRI system in an emergency ambulance setting and that is capable of independent operation without shore power for short periods. Longer periods of operation are possible upon solving alternate power source availability. Use of a low to a mid-field MRI that is suitable to image patients with metal implants or shrapnel, pacemakers and or defibrillators is described. Quick patient positioning and a simple one button push will streamline MRI operation. Use of automated protocol management and post-processing will speed performance. Use of wireless DICOM compatible image transfer will facilitate remote data storage and reading by licensed radiologists. Presence of on-board emergency, neurology and interventional licensed doctors, technicians, emergency personnel and nurses in support of stat diagnosis and clinical intervention is highly sought and intended to benefit patient outcome. Scanning of neonates and small babies is possible on the integrated emergency vehicle MRI diagnosis and intervention system, since the physical clearance and field-of-view (FOV) required for imaging the adult brain are adequate to scan the head, torso and extremity of the pediatric population.

Also described is a novel concept for increasing MRI SNR with a reduced field strength scanner. The concept of reducing the strength of the main MRI component without compromising MRI SNR by concomitantly introducing other sub-components described herein should not be overlooked. All this is possible by exploiting the frequency dependent tissue MR properties (T1, T2), MR sequence parameters (repetition time (TR), echo time (TE), bandwidth (BW), echo train length, number of echo trains, large flip angles, etc.) and MR hardware (near TE=0 imaging capability, fast transceiver, low noise, high signal, low RF and specific absorption rate (SAR), etc.) to reap maximum SNR roughly three-four times achievable by a conventional main magnet field strength MRI scanner or that achieved by a three-fold main magnet field strength conventional MRI scanner. This fresh un-conventional concept is not perceived in the MR community, which believes in increasing the MRI SNR by solely increasing the main magnet field strength (e.g., a 110 ton 10.5T MRI super-conducting magnet with 600 tons of iron shielding weighing more than three times a Boeing 747 airplane and costs roughly $14 million). It is noted that increasing the magnetic field strength from high to UHF adds non-linear size, weight, and cost of installation, maintenance and operation, increases safety hazards and presents $B_0$ and $B_1$ related artifacts and SAR related safety concerns.

In summary, a mature concept for increasing MRI SNR with a reduced field strength 0.5T magnet and strong sub-components is described. Reaping maximum SNR is possible by exploiting the frequency-dependent tissue MR properties ($\downarrow$T1, $\downarrow$T2), MR sequence parameters ($\downarrow$TR, $\downarrow$TE, $\downarrow$BW, $\downarrow$echo train length, $\downarrow$number of echo trains, $\downarrow$flip angles, etc.) and MR hardware (imaging near TE=0 with a fast transceiver, low-noise, high MR signal, low RF and SAR, etc.) at 0.5T. Roughly 3× SNR achievable by a conventional 1.5T clinical whole-body MRI is expected at 0.5T, on diffusion MRI scans, which may be adequate for EMS stroke diagnosis and other mobile brain imaging applications.

An advantage of the system and method in accordance with the invention is it can facilitate early stroke diagnosis necessary to prompt on-site or early intervention or treatment. Another advantage is early on-site diagnosis in remote areas where shore power or electrical grid power are unreliable or may not be available. Another advantage is it can provide service to the global community necessary to identify and treat mental illness with early and serial scanning with response to therapy and or treatment. Yet another advantage of the system and method is it can be used to study brain development in newborns and small babies to determine behavior and cognition in growing children who lack access to standardized healthcare or cannot transport the pediatric subject to a hospital. A further advantage of the system and method is it can safely provide imaging services to refugees crossing borders in temporary camps. Yet another advantage of the system and method is it can be used for on-site field diagnosis and treatment (brain concussion, traumatic brain injury etc.) in soldiers away from residences (homes).

Another advantage of the system and method in accordance with the invention is that they can provide a patient-centered diagnostic imaging system with interventional capability suited to receive mild, moderate or severely ill pediatric and adult patients that is safe to use and provides very high SNR fit for emergency diagnosis in areas remote from a traditional hospital or a healthcare setting.

Another advantage of the system and method in accordance with the invention is that it can provide a SAR efficient RF transmission, optimum reception of MR signals and a small footprint diagnostic imaging system suitable to receive infants to adults and provide optimum care, diagnostics and clinical intervention.

The system and method in accordance with the invention can provide a highly efficient MRI system capable of safe operation to aid stat diagnosis and intervention in an emergency vehicle. The system and method in accordance with the invention can provide a compact, lightweight, liquid helium-free MRI system with a high-performance magnet, gradient and RF chains that can also be placed in any clinical hospital section or stand-alone clinic with minimal installation space restrictions.

According to one aspect of the invention, a magnetic resonance imaging (MRI) system includes: a mid-field super-conducting magnet including a bore and an active shield arranged relative to the magnet; a passive shield arranged relative to the magnet, the passive shield including a first flange arranged adjacent to a first side of the magnet bore; a second flange arranged adjacent to a second side of the magnet bore, wherein the first flange and the second flange are electrically connected to each other, and wherein the passive shield is operative to capture flux extending out from the magnet bore and return the flux to the magnet; an asymmetric head gradient assembly for generating magnetic gradient field in the mid-field super-conducting magnet, the magnetic gradient field being between 100-150 mT/m or having a slew rate between 400-800 T/m/s; a transmit coil; a receive coil; and a controller operatively coupled to the transmit coil and the receive coil, the controller configured to produce an image based on data obtained from the receive coil.

In one embodiment, the gradient assembly comprises a split configuration having a first coil portion and a second coil portion, the first and second coil portions electrically connected in parallel with each other.

In one embodiment, the passive shield comprises a plurality of circular tubes arranged around an outer circumference of the magnet, the plurality of circular tubes connecting the first flange to the second flange.

In one embodiment, the passive shield comprises a plurality of rectangular segments arranged around an outer circumference of the magnet, the plurality of rectangular segments connecting the first flange to the second flange.

In one embodiment, the passive shield comprises a metallic sheet arranged around an outer circumference of the magnet, the metallic sheet connecting the first flange to the second flange.

In one embodiment, the magnet comprise a cryogen-free cooler operative to cool the magnet.

In one embodiment, the mid-field superconducting magnet comprises niobium-titanium-copper wire reinforced with a stainless-steel alloy.

In one embodiment, the system includes a restraining device coupled to the magnet to secure the magnet to a support structure, wherein the restraining device comprises multi-layer magnetic shielding.

In one embodiment, the head gradient assembly includes a noise-attenuating layer, an RF shield, and three-axis windings.

In one embodiment, the MRI system is mounted to a support structure of an emergency vehicle.

In one embodiment, the emergency vehicle comprises a frame to which wheels of the vehicle are attached, and the support structure is attached to the frame via a damper system.

In one embodiment, the damper system comprises a shock absorber, a pneumatic spring, and a liquid bank with dynamic fluid viscosity control.

According to another aspect of the invention, a method is provided for obtaining a magnetic resonance image (MRI) of a head of a patient using an MRI system having a magnet with a bore. The method includes: positioning the head of the patient within the magnet bore; indicating an orientation of a facial feature of the patient relative to the magnet bore; obtaining the MRI image of the patient's head; and modifying the image data based on the orientation of the facial feature.

In one embodiment, indicating the orientation of the facial feature comprises moving a pointer to correspond to the orientation of the facial feature.

In one embodiment, indicating the orientation comprises: performing scout scans of the patient's head; identifying the facial feature in the scout scans; and determining the orientation of the facial feature based on the scout scans.

In one embodiment, indicating the orientation of the facial feature comprises indicating an orientation of a nose of the patient.

In one embodiment, the method includes dynamically adjusting the magnetic resonance sequence based on data obtained from a field camera to remove image phase errors and correct system errors due to shims or gradients.

In one embodiment, the method includes dynamically adjusting for facial motion of the patient based on data obtained from an optical camera to remove patient motion-induced image artifacts.

In one embodiment, the method includes using an anisotropic diffusion MRI phantom to calibrate the MRI system.

In one embodiment, the phantom includes a plurality of vials containing polyvinylpyrrolidone.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

Definitions

The term infant (Latin word infans, meaning unable to speak or speechless) relates to a newborn baby, premature or otherwise and small babies generally from birth up to a year of age.

Radiology procedures relates to non-invasive, resonance and non-resonance imaging tools used for diagnosis, prognosis of illnesses.

Magnetic resonance relates to techniques associated with anatomy, morphology, blood flow, biochemical properties etc. such as imaging, angiography, spectroscopy of the water proton and other metabolites such as phosphorous, sodium, lithium etc. exhibiting magnetic resonance property.

Transport relates to safely moving a baby with its life sustaining equipment and monitoring tools between different hospital sections in search of diagnosis.

Modular system relates to rather quick assembly and disassembly of individual components for ease of installation, de-installation, service, trouble shooting, satisfy design constraints, usability etc.

EMS refers to emergency medical service.

An active shield in an MRI system is defined as a wire or mesh or solid metal sheet or the like energized with internal or external sources and part of the primary, secondary and/or shielding conductors and carrying current intended to modify, alter, curb or mitigate propagation of the main field generate by one or many wires or mesh or solid metal sheets or the like.

A passive shield in an MRI system is defined as a wire or mesh or solid metal sheet or the like not energized with internal or external sources and part of the primary, secondary and/or shielding conductors and carrying current intended to modify, alter, curb or mitigate propagation of the main field generate by one or many wires or mesh or solid metal sheets or the like.

A cryogen-free cooling system in an MRI system is defined as an enthalpy exchange system without the use of solid, liquid or gaseous medium intended to relieve or absorb heat with the host, contact medium such as the cryo-cooler and its cooling accessories, such the compressor and/or pumps.

A mid-field magnet is defined as a magnet having a field between 0.3-0.7T.

BRIEF DESCRIPTION OF DRAWINGS

In the annexed drawings, like references indicate like parts or features.

FIG. 4A illustrates the use of cylinders, FIG. 4B illustrates the use of straight segments, and FIG. 4C illustrates the use of solid sheet lining, in accordance with the invention.

FIG. 7B schematically illustrates an exemplary hardware scheme for identifying the orientation of a patient in the MRI system.

FIGS. 8A and 8B illustrate different cross-sectional views of an MRI magnet assembly in accordance with the invention.

DETAILED DESCRIPTION OF INVENTION

Figure 1:
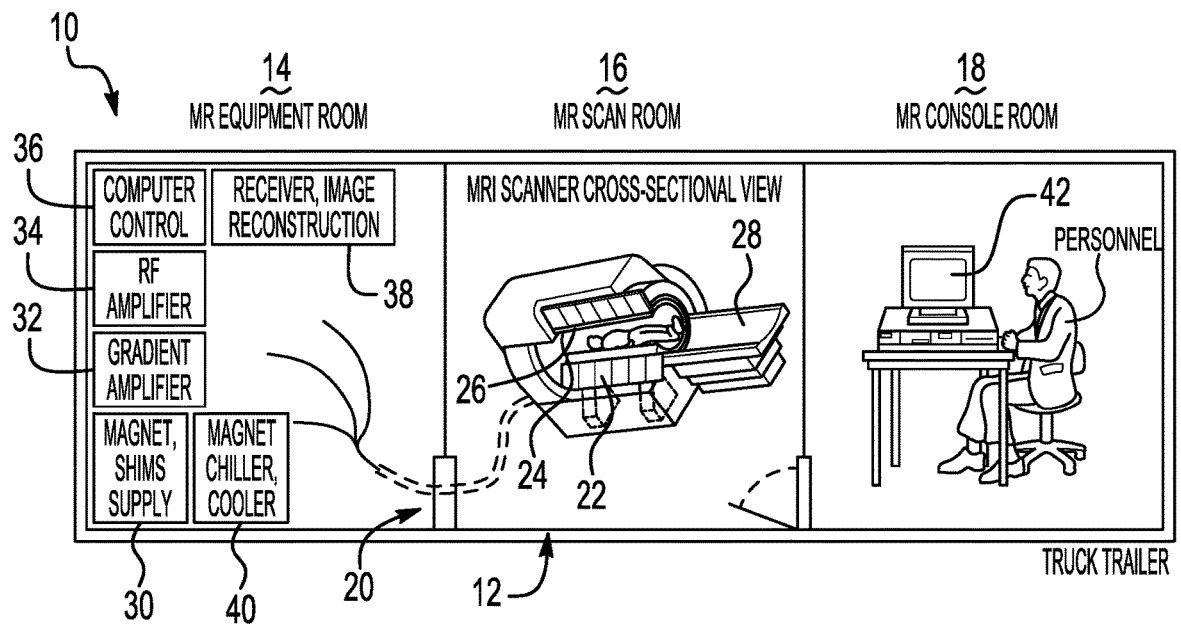
FIG. 1 is a simple schematic diagram of a 1.5T whole-body MRI system installed in a commercial truck.

Embodiments of the present invention will now be described with reference to the drawings, wherein like reference numerals are used to refer to like elements throughout. It will be understood that the figures are not necessarily to scale.

Referring to FIG. 1, illustrated is a diagram of a conventional truck-trailer MRI system 10 with an RF shield 12, equipment room 14, scan room 16 and MR console room 18. The system includes a magnet, gradient coils, body RF coil, patient imaging set up, computer control for MR sequence programming, exciting and receiving MR signals, digitization, reconstruction, post-processing and display on the MR computer console. More specifically, the scan room 16 includes at least an RF shield 12, penetration panel 20, main magnet 22, gradient coils 24, RF body transmit coil 26, RF receiver arrays and MR patient table 28. The equipment room 14 includes at least the penetration in-line radiofrequency (RF) and intermediate frequency (IF) filters (not shown), magnet and shim supplies 30, gradient and RF amplifiers 32, 34, and control/monitoring circuits 36, 38. Further, a magnet chiller and water and air coolers 40 for cooling equipment are utilized. The MR console room 18 includes a computer system and display 42 with operator functions to control and run the MRI scanner, process and archive images, and camera equipment to record scan room activity and patient communication etc. As can be appreciated, due to the size and weight of such truck-trailer system, the mobility of the system is limited.

Figure 2:
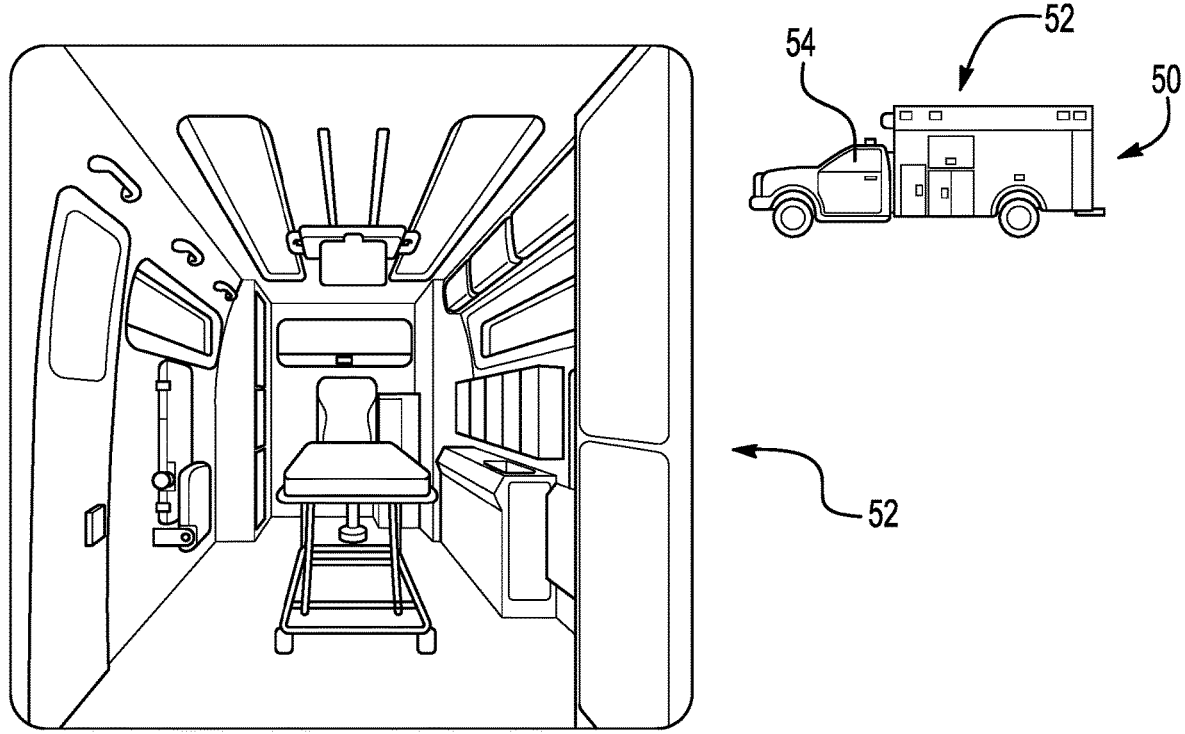
FIG. 2 is a side view of an emergency ambulance and a perspective view of a patient section within the ambulance.

FIG. 2 is side view of a conventional EMS ambulance system 50 along with a perspective view of an interior portion of an emergency section 52 of the ambulance 50. The EMS ambulance system 50 includes a driver section 54 in which a driver can operate the ambulance 50. The emergency section 52 includes an inverter for providing AC power, a mobile stretcher, physiological monitor, medical air/oxygen tanks, fluid infusion equipment, blood-clotting and de-clotting equipment and drugs, catheterization supplies and drugs, telemedicine hookup, and other emergency medical supplies necessary for prompt emergency care.

It would be advantageous if an MRI system could be placed in an EMS ambulance, as this would provide portability of an MRI system. However, and as briefly discussed below, conventionally there have been barriers that have prevented placement of an MRI system in an EMS ambulance.

First, there are barriers for MRI installation. A majority of the barriers pertain to the scanner size, weight, required footprint (space) and fringe fields. Excessive scanner size and foot-print may not support ambulance transport, whereas excessive weight may impose restrictions to the vehicle size and can limit the distance the ambulance can travel, which can make it unable to reach locations where help is needed. Whereas excessive fringe fields with the 5 Gauss (G) lines extending past the ambulance emergency patient section can be hazardous, as it may attract ferro-, dia- and para-magnetic materials into the magnet, affecting diagnosis and treatment.

Excessive fringe fields can also interfere with vehicle functions and medical equipment in proximity of the scanner inside the emergency vehicle.

Second, there are barriers to MRI operation in an emergency ambulance. A majority of the barriers relate to choice of a magnet and power, ramp-up and ramp-down times, ability to operate in a vehicle with motors, etc. and survive vibration and shock experienced during the ride. Choice between a permanent, resistive electromagnet and superconducting magnet systems must be made, such that the system is appropriate for an emergency ambulance including the power required for sustained magnet operation. A magnet is ramped to field where an MRI exam can be safely performed. The same magnet is de-ramped when not in use to save power and to mitigate adverse events in the case of an emergency necessitating immediate shut down. The magnet must safely operate inside a vehicle equipped with an engine, ferro-magnetic materials and moving parts etc. The MRI system and its components should be light-weight and capable of sustaining shock and vibration due to the vehicle changing lanes, making turns and going over speed bumps, i.e., when the EMS vehicle is mobile.

Third, there are safety barriers. These include instant cryogen venting, quick magnet ramp and de-ramping ability, overcome body stimulation thresholds, low radio frequency (RF) power absorption without causing SAR issues during an MRI exam, and scan patients with special conditions. Instant venting of cryogens during a magnet quench is necessary to preserve the oxygen available in the emergency ambulance section (i.e., welfare of the patient and personnel). To preserve safety, it is preferable to provide quick ramping to field where an MRI exam can be performed and quick de-ramping to 20 mT per IEC 60601-2-33 MRI specific standard, in the case of a forced shut-down during an emergency. The ability to use strong and fast gradients to enable diffusion weighted imaging (DWI) and faster MR imaging sequences should not exceed current body stimulation thresholds (40 mT/m field strength, 150 T/m/s slew rate) and human electric field stimulation thresholds for peripheral nerve stimulation (human nerve dia 20 μm electrical stimulation electric field thresholds are in the order of 6-20 V/m and pulse duration in the range of 50-800 μs). The MRI exam should not exceed the Food and Drug Administration (FDA) SAR limits for RF power absorption of 3.2 W/Kg in the human brain. Should SAR limits be exceeded, the scan should be paused to allow SAR reduction while prolonging the MR exam, which is not practical for imaging stroke patients. It is important to scan patients with guidewires and metal implants, and patients with active implantable medical devices (AIMDs) like pacemakers, defibrillators, etc. without damage to the patient and/or overheating per ASTM F2182-11a and ISO/TS 10974:2018 standards.

Fourth, several performance barriers must be overcome to safely operate a MRI scanner in an emergency ambulance. These barriers are mainly high magnetic field, DWI compatible MRI hardware, low gradient eddy current induced acoustic noise (<99 dBA), low RF SAR and high MRI SNR. High magnet field strength is necessary to provide high MRI SNR, since SNR is directly proportional to the main magnet field strength. This has led to the imaging movement to high field (1.5T, 3T) and ultra-high-field (UHF, 7T and 10.5T research) MRI magnet systems. Moving to high and UHF is accompanied with expensive magnet installation (at or below grade to avoid building vibrations reaching the magnet), greater power requirements, elevated $B_0$ and $B_1^+$ related issues, which are difficult to tackle and not suitable for transport. DWI compatible MRI hardware is necessary to satisfy stroke imaging requirements recommended by the AHA/ASA, but without exceeding the stimulation thresholds which is also difficult, since at higher field strengths wider bandwidth pulses are required to cover the same slice widths (or ppm scale). Use of narrow pulse-width (10-50 μs), high amplitude (>50 μT) RF pulses to improve slice profiles, increase frequency bandwidth are possible without exceeding SAR. Since diagnosis depends on the MR image quality, high image SNR and resolutions will aid non-invasive diagnosis, without the use of ionizing radiation. High MRI SNR is also required in expected in six-seven minute exam times to compete with current MSU CT imaging practices on stroke patients.

Figure 3:
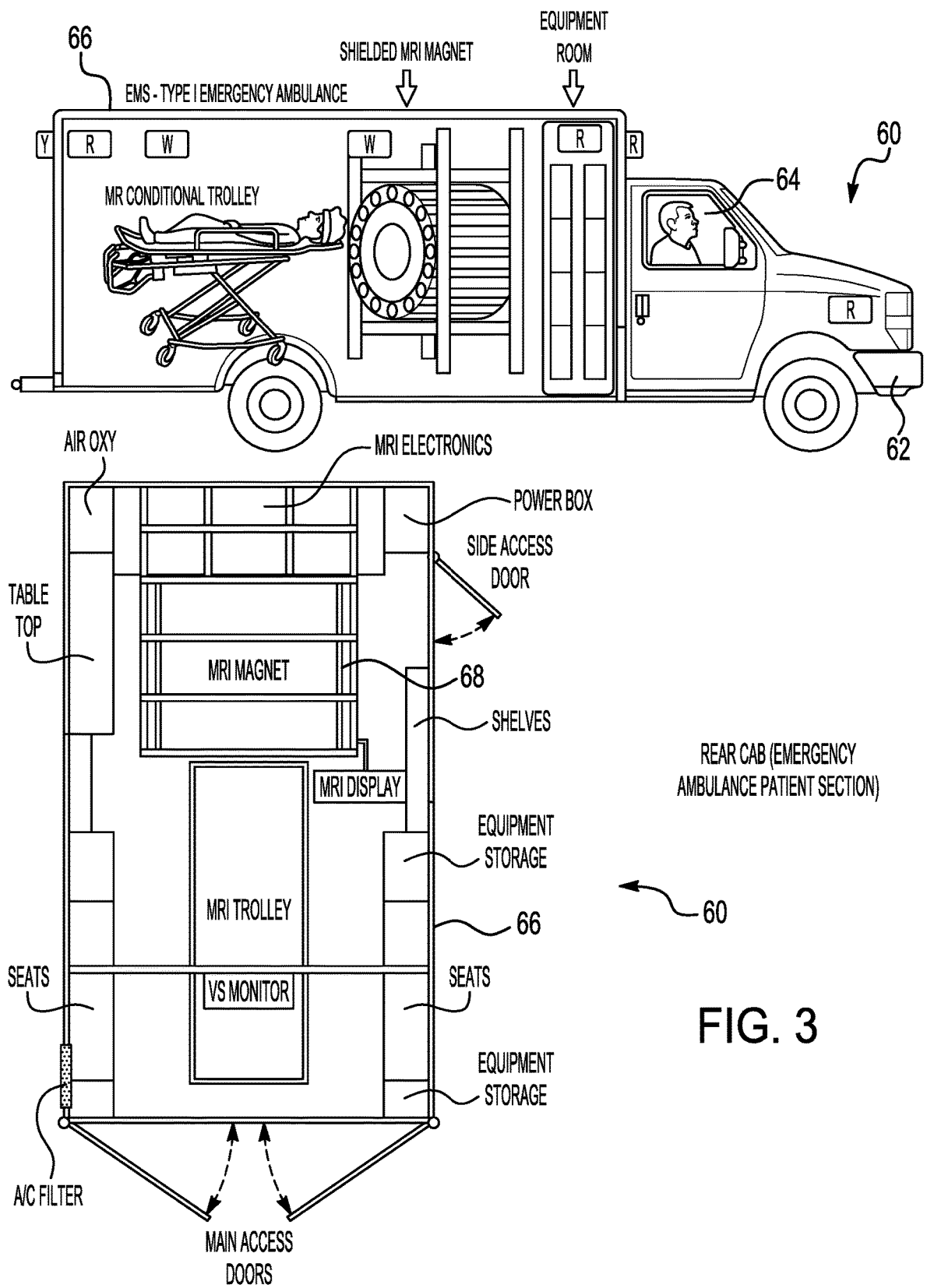
FIG. 3 is a side view of an EMS ambulance and a top schematic view of a patient section of an emergency ambulance in accordance with the present invention.

FIG. 3 illustrates a preferred embodiment of an MRI system 60 in accordance with the invention that provides an EMS ambulance with MRI capability. The MRI system 60 includes diagnostic MRI equipment inside an EMS ambulance 62 that is capable for handling local and remote emergency applications. The emergency ambulance 62 is split in two distinct sections, a first section 64 carrying the driver and physicians and a second section 66 carrying the generator, diagnostic MRI equipment, emergency equipment, accessories (e.g., vital signs monitor etc.), and healthcare personnel. Splitting into sections is advantageous for isolating the front-cab (first section 62) from the emergency section 64 (rear cab) to prevent shock and vibration from passing through to the emergency section 66, thereby protecting the emergency section 66 to an extent from accidents and collisions initiated from the frontal portion of the emergency vehicle 62. Type I or III emergency ambulances in the United States of America with weight bearing capacity between 4,000 to 6,000 lbs. (1,818-2,727 Kgs) are preferred, although, depending on the MRI magnet field strength, size and overall system weight (including support accessory and human personnel), the final weight bearing capacity can be adjusted accordingly based on the emergency ambulance vehicle class.

An emergency section 66 of approximately 14 ft. in length and approximately 8 ft. in width suited for Type I or III emergency ambulance vehicles in the USA is preferred. It is noted that emergency vehicle class and sizes vary slightly globally. In these cases, care must be taken to ensure safety is not compromised.

A self-shielded, super-conducting MRI magnet 68 with a cryocooler head and a 5 gauss (G) line distribution is arranged within the ambulance, with the emergency section 66 housing acting as an RF shield representing a combined Zone III and IV, per widely recognized International Electrotechnical Commission (IEC) 60601-2-33 MRI specific safety standard. Although the preferred magnetic field should be as high as possible, it should be obtained to satisfy the 5G criteria, else MRI Zone IV criteria may not be maintained inside the emergency ambulance 62. A custom lightweight, liquid helium-free, cooled low fringe field magnet-based MRI system that implements rapid ramping and de-ramping to zero field ability, high performance gradients and RF systems, specifically with a SAR efficient transmit and high SNR imaging devices (RF coils), is preferred. The quick-ramping from OFF to ON is made possible due to the efficient cooling of the magnet along with the use of higher charging current (200-300A or greater for this size magnet), higher current carrying conductors (e.g. 30% better) and efficient cooling of the magnet. In this regard, the cooling is such that the temperature differential inside a vacuum chamber of the magnet (the vacuum chamber surrounding the conductors of the magnet) between the active state and the inactive state is reduced by a factor of eight relative to a conventional MRI system. Additionally, the arrangement of conduction cooling fingers around the magnet and a combination and arrangement of the vacuum chambers around the primary and secondary magnet windings elongates the temperature conduction path, which minimizes the temperature gradient drop-off (i.e. 4K to 10K, to 40-50K, 100K and possibly higher). The temperature conduction path is elongated in order to minimize the gradient (or change) in cold-mass temperature in the magnet structure. A lower temperature gradient provides a stable design, which can prevent over-heating that leads to a magnet quench with loss of superconductivity in the current carrying magnet wires. As such, conductor performance is enhanced (e.g., 30% increase) and current can be ramped at a much higher rate, resulting in the magnet being brought online in significantly less time relative to a conventional magnet.

A nominal main magnet field strength of 0.5±0.2T for the adult head MRI is practical, although with improved magnet materials and technology, a higher field strength magnet can be integrated safely. Since the magnetic pull will be less than one-third a comparable size 1.5T brain magnet and even less than the 1.5T whole-body magnet, and with one-ninth RF of a comparable size 1.5T head magnet and even less than the 1.5T whole-body clinical MRI, use of a low-to-mid field brain MRI is ideal to image patients with metal implants, shrapnel, pacemaker and defibrillator. In this regard, the patient will experience minimal to no RF heating when imaged using a mid-field strength MRI scanner exhibiting low RF and SAR. In addition, patients with AIMDs can also be safely imaged per the abovementioned ASTM and ISO/TS standards, safely extending high SNR diagnostic MRI to emergency applications. Owing to the cryogen-free cooled magnet design (and thus the absence of the helium chamber), the overall magnet size (which includes reinforced high current carrying NbTiCu magnet wire conductor) can be compact.

The MRI magnetic as described herein is capable ON-OFF switching with stringent fields (5 Gauss <1 m). The compact, lightweight design of the magnet overcomes MR installation barriers in an ambulance, whereas the stringent fringe fields and switchable features swiftly overcome operational safety barriers. The proprietary fast-charge-discharge design permits switching between idle-mode and full-field (0.5T) in 2-4 minutes, which is suitable for EMS applications, and from 0.5T to 20mT in less than 10 seconds, favorably mitigating magnet-related adverse events. The MRI magnet can be switched OFF with 100% power savings when not in use and switched to full field, i.e., turned ON from 0T to 0.5T, in 5-10 minutes. Rapid magnet switching favors magnet installations in busy clinical settings, such as in the surgery suite, emergency ward, stand-alone clinics, ambulances, etc.

Careful exploitation of the frequency dependent tissue MR properties, MR techniques and hardware resulting in an innovative compact, low-cost MRI scanner is preferred over high field systems to enhance safety in an EMS world. Specifically, the use of lower magnetic field strength magnets with high performance gradients and RF systems and comparable SNR available at three times the magnet field of conventional MR systems is preferred for fast-imaging in EMS stroke applications. The use of quieter, safer and improved performance superconducting magnet systems with reduced footprint, within an emergency vehicle setting is advantageous. Offering stat diagnosis and clinical intervention prior to hospital transport can eliminate additional stress, after which the remaining residual risks are well acceptable to the caregiver. In most cases, the benefits of immediate diagnosis and clinical intervention with an emergency vehicle system outweigh the abovementioned risks, in the best interest of providing needed clinical care to the patient.

Use of a light-weight permanent magnet, resistive and superconducting magnets requiring minimal power are preferred. A permanent magnet becomes heavier as the field strength increases and soon becomes unsuitable for ambulance transport. Main magnetic field drifts common to resistive magnets are also unsuitable for imaging. Cryogen-free superconducting magnets requiring very minimal maintenance are suited for remote operation, so long as the required power is supplied to sustain the MRI main magnetic field strength. The use of cryogen-free, field-switchable superconducting magnets are preferred as they are ideal for use, although, lighter permanent magnets made with newer materials capable of holding higher field strengths and low-energy field-stable resistive magnets can also be used.

A compact, light-weight superconducting magnet choice of 0.3-0.7T with quick ramping to field in 5 minutes and de-ramping to zero field in less than 20 seconds is preferred to present a high enough field strength for providing high MRI SNR with a practical design suited for EMS use. Cryogen-free magnet technology obviates the need for a helium chamber which shrinks the magnet size. The lack of helium also precludes the use of special venting methods, mandatory with cryogens. In addition, the use of insulated composite niobium-titanium-copper (NbTiCu) wires reinforced with the higher elastic modulus stainless steel alloy 304 cladding to increase the winding pack current density by 30% which further reduces the overall magnet size. In addition, soft, noise-less, cryogen-free, un-eventful magnet ramping, de-ramping or quench does not startle the patient or personnel in the EMS vehicle.

Reducing the main magnet field strength will alter the MR related tissue properties and mainly reduce tissue T1 (spin-lattice relaxation time) which in turn will drastically reduce repetition time (TR) and help with MRI signal averaging intended to increase MRI SNR. Reducing the main magnet field strength will also lengthen (spin-spin relaxation time) T2 values and increase the MRI signal acquisition window. In addition, reducing the main magnetic field strength will shrink the fringe field to roughly 1 m for 5 G lines on a 0.5T MRI. With additional passive magnet shielding the naturally present 5 G lines will reduce from 1 m to roughly 0.5 m (<2 ft) of the magnet surface and enhance $B_0$ related safety, which is well suited for an EMS application. Installation of DWI compatible strong connectome gradients (100-150 mT/m) and faster slew rates (400-800 T/m/s) will facilitate short echo time (TE) and shorter single echo trains based MR signal acquisitions with faster gradient encoding. Specific to MRI, the IEC/ICNIRP normal mode dB/dt (magnetic field rheobase) operating limit of 80 T/s for gradient output corresponding to an effective stimulation duration ($t_{s,eff}$ or chronaxie) of 120 µs using dB/dt=20 $(1+0.36/t_{s,eff})$ $Ts^{-1}$ (expressed in %) is set at one-third the rheobase electric field of 2 V/m for PNS (safe conservative limit). With a maximum $t_{s,eff}$ of 55 µs, the intent is to exceed the IEC whole-body limit (80 T/s), corresponding to 151 T/s per the above hyperbolic equation for dB/dt, but only in the human brain for which no thresholds exist. Since the RF power reduces as square of the operating frequency (or field strength), with $1/9^{th}$ RF power at 0.5T in comparison to 1.5T, SAR is very hard to exceed at one-third the field strength. Very narrow (10-50 µs) pulse-widths and wide bandwidth RF pulses facilitate better slice profiles without exceeding FDA SAR limits for RF power deposition in humans.

Figure 4A:
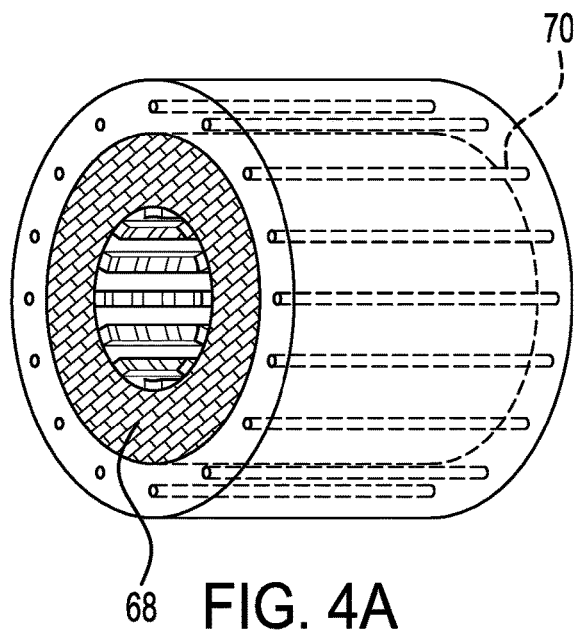
FIGS. 4A-4C illustrate exemplary embodiments of a passive shield for the magnetic field of the MRI magnet.
Figure 4B:
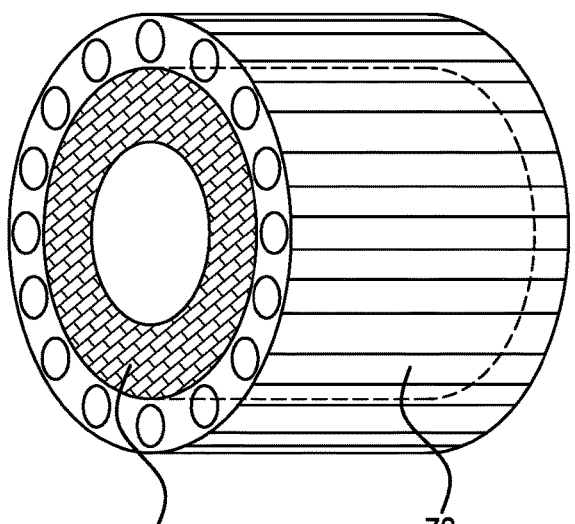
Figure 4C:
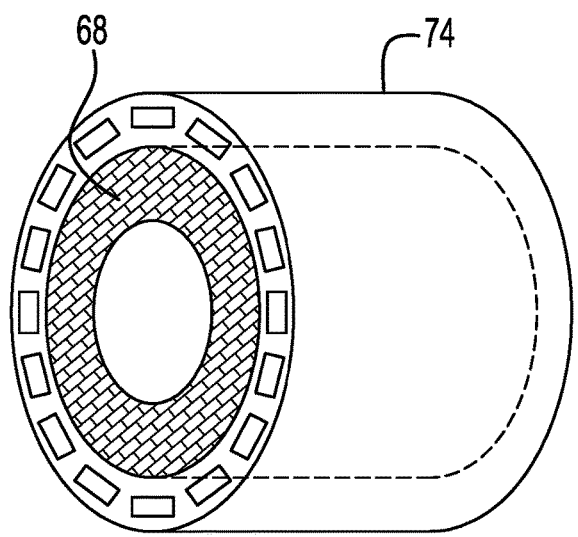
Figure 4D:
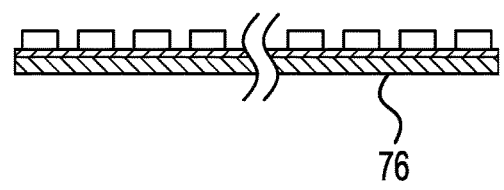
FIG. 4D illustrate a shim strip with individual metal shims in accordance with the invention.

Moving to FIGS. 4A-4B, illustrated are three examples of passive shielding for the magnetic field of the actively, self-shielded MRI magnet 68 of FIG. 3. FIGS. 4A-4C are substantially the same except for the type of passive shields. While FIGS. 4A-4C show specific type of passive shields, other types of shields are possible. The passive shielding, in combination with active shielding (the active shielding formed from primary and shielding coils integrated within the structure), is intended to further reduce the magnet's fringe fields. FIG. 4A includes sixteen circular tubes 70, FIG. 4B includes 16 straight segments 72 (which are located outside the magnet) and FIG. 4C includes solid sheet 74 connecting the front and back opening of the magnet bore around the magnet. The sixteen cylindrical cross-sectional tubes 70, straight-segments 72 or solid-sheet 74, which may be made of ferromagnetic or diamagnetic materials (iron yoke or steel weighing<10% of the main magnet) are lined outside and attached to the magnet and/or magnet frame and are intended to capture flux extending out of the magnet volume and return the flux back to the superconducting magnet. This is so done to preserve the system magnetic flux or magnetic field energy without significantly diminishing the main magnet field strength over the imaging volume while exhibiting minimum interaction with neighboring equipment operating in the vicinity of the magnet. A partial, cross-sectional view of one room temperature magnet shim tray 76 of FIG. 4A is shown in FIG. 4D is intended to homogenize the main magnet field strength homogeneity over the imaging FOV to <50 ppm.

In capturing the flux, a majority of the flux terminating on the passive shield tends to direct current to aid the main magnet field, and some to provide shielding effect due to Lenz's law with nearly net zero field outside. The current aligned with the main magnet field will help to direct the flux in the same direction as the main magnet while the current opposing the main magnet field will provide shielding by canceling the net current on the outer surface of the shielding material, i.e. no net field outside the shielding material, thereby providing adequate shielding without significantly diminishing the field inside the magnet.

Additional magnetic shielding, if necessary, to restrict the MRI magnet fringe field to 5G or less inside the emergency vehicle chassis can be achieved using high permeability (µ) material plates. For example, with 0.06-0.125" thick iron (0.25 H/m) or electrical steel plates (0.005 H/m) or high-p material (0.025-0.063 H/m), (see FIG. 5B, which is discussed in further detail below). Spacing, for example of 5-10 mm, between successive plates will enhance magnetic shielding efficiency. Proximity of the shielding metal layers will give rise to eddy currents which can affect MR images. MR sequences will be modified to compensate for the known eddy currents to eliminate slice shifting and image artifacts and, by other means specified on the MRI System section and discussed below with respect to FIG. 10. To maintain safety, all emergency accessories maintained inside the EMS ambulance 62 should be non-magnetic to the extent possible to avoid projectile mishaps. Slightly magnetic (or MR Conditional) equipment and accessories should be tethered to the EMS ambulance 62 to avoid MRI adverse events. All display and computer peripherals and accessories used in the system 60 are MR Safe or MR Conditional. Stationary accessories can be RF shielded, and all active equipment signals can be filtered to eliminate inter-equipment interferences and to produce artifact free high SNR MRI images.

The housing of the emergency section 66 serves as an MRI ground and all peripherals can be connected to the rear-section vehicle chassis. The MRI magnet 68 can be lifted off ground and held to the restraining mechanism, to align the magnet iso-center to the patient head held on the MR Conditional emergency trolley. The MR magnet and related equipment can be shielded and stored underneath and behind the magnet. The weight of the MR magnet and related equipment is preferably distributed but centered to the extent possible between the load-bearing wheels towards the ambulance center. The generator and MR equipment can be surge-protected to better isolate equipment ground from the earth ground to prevent lightning strikes and to minimize ground leakage currents when the EMS ambulance 62 is connected to shore power. This may be accomplished with a floating input (or in other words, floating or differential or balanced power from the generator or shore power) driving the emergency section 66.

Figure 5A:
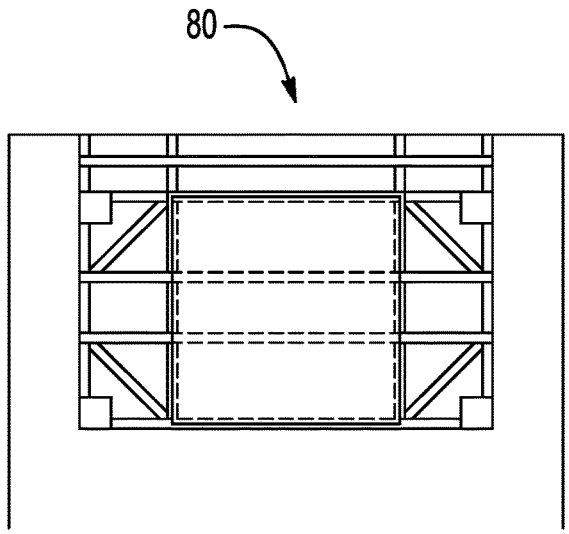
FIGS. 5A-5C are partial top, side and rear views, respectively, illustrating various means for restraining the MRI magnet (and other equipment) in the patient section of the ambulance in accordance with the invention.
Figure 5B:
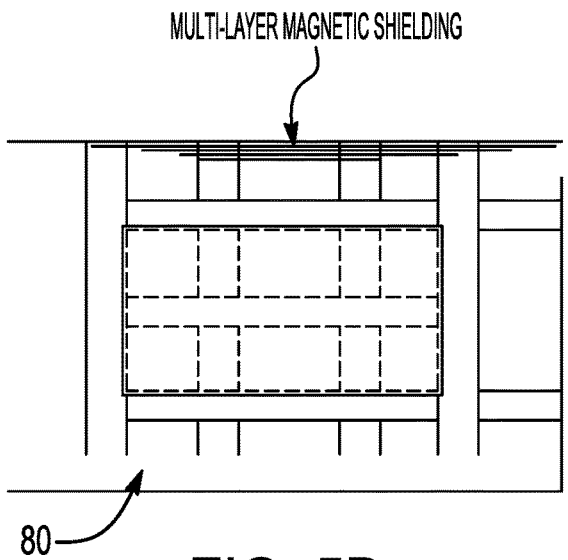
Figure 5C:
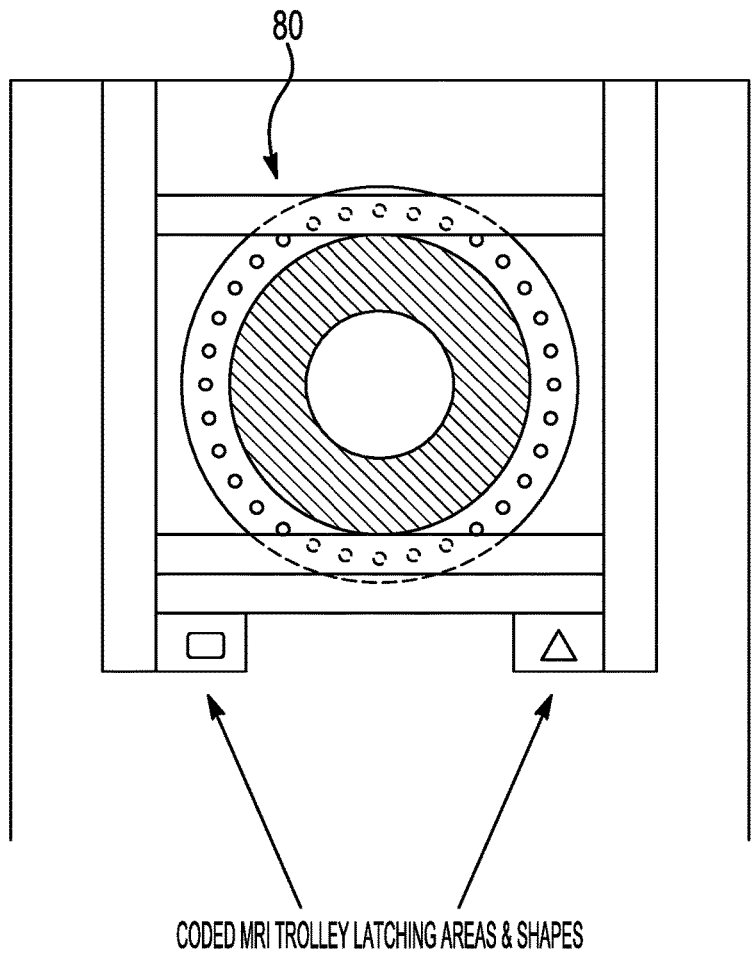

With reference to the three sided partial views of the second section 66 as shown in FIGS. 5A-5C, rectangular and square cross-sectional 'H' and 'V' style support beams 80 are employed as holding and restraining mechanisms for the magnet 68 and the electronics. The holding and restraining mechanisms 80 provide displacement-free protection during driving and minimize the likelihood that the EMS ambulance 62 may tip over, particularly when changing lanes or making turns. This is done such that the vehicle weight will always remain very close to its physical center and a majority of the ambulance weight is oriented towards earth's gravity at all times during movement of the ambulance.

Figure 6:
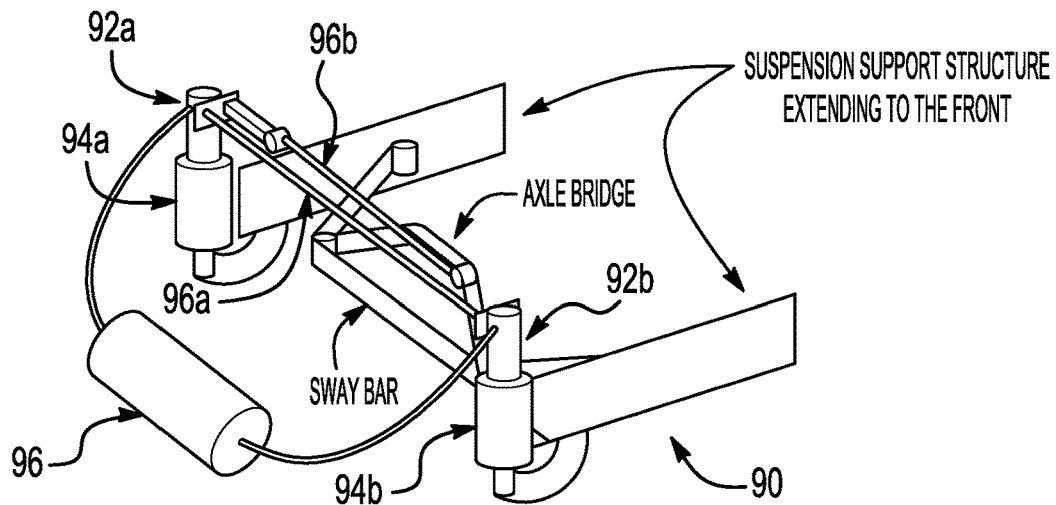
FIG. 6 illustrates an exemplary suspension system for the patient section of the ambulance in accordance with the invention.

With reference to FIG. 6, the second section 66 of the EMS ambulance 62, which houses the MRI and accessories, human personnel and emergency equipment, has a custom suspension system 90 (rear suspension) to provide a smooth ride, thereby protecting equipment and personnel in the second section 66. Each shock absorber-vibration dampening component preferably has at a minimum at least 6,000 lbs. weight bearing capacity and a maximum 2× the emergency section weight capacity. The equipment and personnel are held in place by the suspension system 90, which includes multiple liquid-filled integrated shock absorbers 92a, 92b and vibration-dampening pneumatic springs 94a, 94b. Additionally, a liquid bank 96 with a computer controlled gyroscope-feedback circuit and dynamic liquid viscosity altering current control offers superior shock absorption, vibration dampening and anti-roll, thereby offering a soft, shock-free stable ride. The custom suspension system 90 is strengthened with cross-members 96a, 96b. Doing so will satisfy a primary aim of the suspension system 90, i.e., a) to center the ambulance weight towards the center of the vehicle 62 and b) to orient a major portion of the weight towards gravity during motion.

Combinatory use of non-Newtonian or thickening fluids or Bingham plastics that become liquids at high pressure can be used. Use of magneto-rheological dampers are not preferred, as the electro-magnet can become saturated from the MRI stray magnetic fields in the emergency ambulance during the life of the equipment. However, with sufficient magnetic shielding such materials can be used cautiously.

It is not necessary to customize the front suspension system of the EMS ambulance 62, but any modification can help ease the shock and vibration felt by the driver and clinical personnel. For example, the use of passive anti-roll bars between the suspension and the chassis and between the front wheels can help to resist body roll during cornering. When operating the MR system, and if necessary, two or more support legs can be extended from the EMS ambulance 62 to the ground to establish a temporary, solid foundation for the second section 66 (rear cab).

In summary, the use of active and passive suspension and feedback means are intended to prevent ambulance lean during turns and to provide a smooth ride that protects equipment and personnel on-board the ambulance 62 during an emergency run. In all cases the Federal specification for star-of-life ambulances, namely KKK-A-1822 should be maintained for the integrated diagnostic interventional emergency ambulance system.

A 120V/230V/277V/480 VAC single or three phase 10-15 kWh generator powered by natural gas, diesel or by other means (solar, wind power with conversion electronics, etc.) can provide the required AC and DC power for a total of anywhere between 3-8 kWh at all times, sufficient to operate the equipment, accessories and required air-conditioning or heat (depending on the ambient environment) in the second section 66. Specifically, the generator can power the air conditioning with 120 VAC (or 230 VAC) to satisfy 2010 EPA (or world) requirements and preferably maintains a 35° temperature differential to the ambient temperature. Since the EMS ambulance battery power and alternator may be independent of the emergency section, the generator, its power and therefore the emergency medical equipment can be ON at all times.

An MR conditional custom trolley at its maximum height can latch to the magnet restraining mechanism such that the patient head is centered at the magnet iso-center, without direct latching to the magnet (see FIG. 5C) in or near the imaging FOV. Any latching can delay trolley disengagement from the magnet which can perturb emergency care and thus is not desirable. The trolley can be unlatched from the magnet restraining mechanism with a foot or hand lever attached to the trolley. Head straps and foam pads can be integrated to the trolley to further minimize or eliminate patient motion during the MRI exam.

Figure 7A:
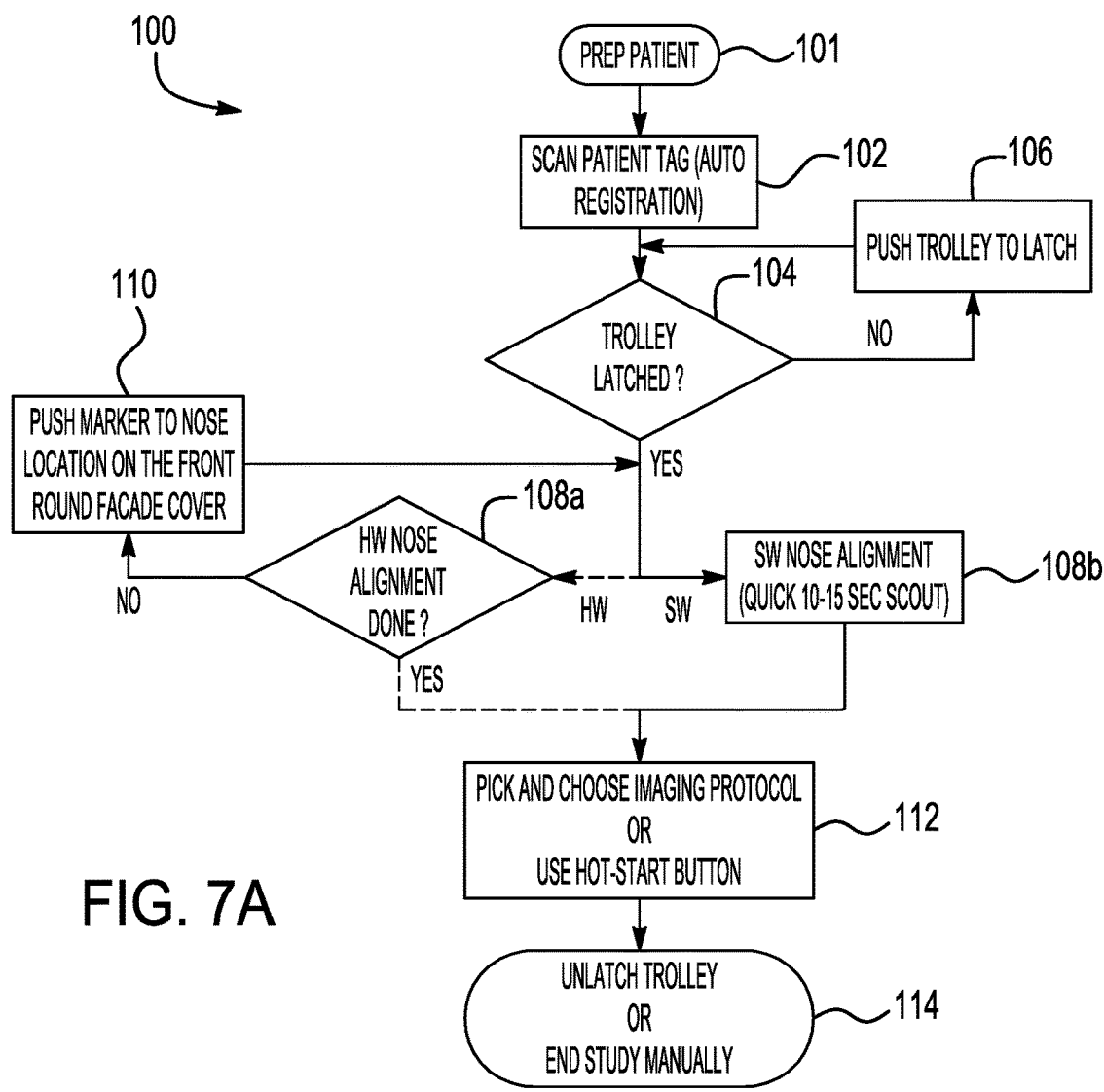
FIG. 7A is a flow chart illustrating exemplary steps for operating an MRI system in accordance with the invention.

With reference to the flowchart 100 of FIG. 7, illustrated are exemplary steps for conducting an MR exam with a stationary EMS ambulance 62. Beginning at step 101 a patient is prepped by placing him/her on an MR trolley and the trolley can be latched on to the magnet restraining system by engaging the like trolley dimensions (square, triangle) into the system (see also FIG. 5C). Once latched the patient head will be in the imaging field of view of the symmetric solenoidal magnet and asymmetric gradients necessary to center the brain. Based on the head RF coil design, the magnet cylinder may be left open or closed along the magnet axis (Z).

Next at step 102, the patient information is scanned using, for example, a hand-held scanner to scan information from a patient tag. The scanned information is used to associate the collected image data to the actual patient being imaged. Next at step 104 it is determined if the trolley is latched in the scan position. If the trolley is not latched, then the method moves to step 106 where the user latches the trolley and the method moves back to step 104. If at step 104 the trolley is latched, then the method moves to step 108a or 108b depending on if a hardware or software alignment of the patient is to be performed.

A majority of patients will be imaged head-first and in a supine position. In cases where the patient cannot lay supine, a hardware or software intelligent nose-position marker system-based image adjustment can be made on the patient position (left-, right-lateral or prone), respectively.

If a hardware alignment is performed as indicated at step 108a, then at step 110 the orientation of the patient's nose is identified to the system. For example, and with reference to FIG. 7B, hardware based adjustment may be implemented by orienting a pointer 122 of a rheostat 120 on a front façade cover of the MR console 42 to be aligned with the patient's nose, i.e., head-supine shall be 12 Noon (total resistance of 12 kilo ohm between points A and B, for example), whereas prone will be 6 PM (six kilo ohm for example) with reference to a clock. Movement of the pointer alters the resistance between terminals A and B, which can be used to identify the position of the pointer (and thus the orientation of the patient). Once aligned, the method then moves top step 112.

If a software alignment is to be performed, such software alignment can be based on the brain and nose septum, which can be identified via processing of scout images (which take approximately of 10-15 seconds to obtain and process. In the preferred embodiment, the embedded receive RF head coil array in the MR system can be used to receive MR signals from the human anatomy. Once the patient alignment is determined, the method moves to step 112 where various scan settings are selected and a scan is performed. Once the scan is complete, then at step 114 the trolley is unlatched and the patient is removed from the MRI scanner.

MR sequences provided by the manufacturer and edited by the user can be stored in protocols, which can be accessed at any time. All protocols will be displayed on the user interactive screen, of which one protocol shall be chosen at a given time by the healthcare personnel. Once chosen, the MRI scanner can run automatically unless stopped or paused by the user. Alternatively, a hand-held hot-start push-button will enable start, pause or stop of the MR scan. At the end of each MR sequence, raw data and images can be pushed over to the resident hospital network with DICOM and HIPAA compliance. Data may also be stored at the host computer on the emergency vehicle MRI for redundancy. When not in use, the ambulance can be locked to prevent data breach of the host computer. The host computer can also be under lock and key. Images may be displayed on the interactive MRI screen if necessary. Image post-processing can be automated to save time and diagnosis by a certified radiologist. User post-processing steps can also be automated to streamline MRI operation. Removal of the trolley from the MR system will end the MR study, which can otherwise be closed by the operator.

A cryogen-free, cooled magnet is secured to a restraining mechanism of the second section 66 with fasteners such as metal screws (not shown). With reference to FIGS. 8A and 8B, the magnet system 130 will house room temperature shims 132 (analogous to the shim tray 76 in FIG. 4D), connectome head gradients (cHG) 134, the RF shield 136, volume transmit RF 138 and multi-channel receive RF head coil array 140. The 16-32 section shim trays (FIG. 4D), with each section further divided in to 12-48 sub-sections, each sub-section carrying one small piece of grain-oriented steel, will help to homogenize the main magnet field to <50 ppm over the imaging region-of-interest (ROI).

The magnet-gradient assembly inner bore diameter (excluding the RF body coil-shield) of 38-46 cm and outer diameters of 80-120 cm operating between 0.3-0.7T is preferred. Use of reinforced copper wire is preferred, although use of niobium-titanium or niobium-tin, low, mid (e.g., $MgB_2$) or high temperature superconducting (e.g., rare earth barium copper oxide (ReBCO), bismuth-strontium-calcium-copper-oxygen (BSCCO)) wire with high current carrying density of 100 $A/mm^2$ or greater can be used. A compensating $B_0$ axis-oriented solenoid coil superimposed over the gradients will help to dynamically compensate slice shifts due to eddy currents.

Self-shielded, gradient design can be "thumb print" minimum inductance (see Turner et al. (Turner, R. Comparison of minimum inductance and minimum power gradient coil design strategies. In: Book of abstracts: Eleventh Annual Meeting of the Society of Magnetic Resonance in Medicine. Berkeley, Calif.: ISMRM, 1992: 4031, incorporated herein by reference in its entirety)). However, other designs are possible. First order shimming of the main magnet field is possible by superimposing small DC currents (0-20A) over the corresponding gradient coils to further homogenize the field over the imaging FOV.

An asymmetric, minimum-inductance split head gradient design for low voltage-high current drive is implemented to reduce the GPA drive voltages that drive the split-head gradient X, Y, and Z coils to one half of the conventional value, i.e. from 800V down to 400V (the split voltage design operates at the same current but at half the voltage as a conventional design). Such operation is possible because the split configuration, which comprises a first coil portion and a second coil portion electrically in parallel with the first coil portion, reduces impedance by 50%. Thus, the split coil configuration requires half the voltage to produce the same current as a non-split configuration. This enables the custom 400A-400V GPA and drive the gradients (DC-DC drive) to be powered with the 403.2V, 100 kWh Tesla X, Panasonic battery, without compromising gradient performance. By avoiding the traditional AC-DC conversion at high power (13 kW), savings up to 3.9 kW can be realized by minimizing the 0.7 power-factor based 30% losses from the AC to DC conversion processes. Also, novel use of low-inductance copper tubes permit efficient cooling when operating at 101 mT/m maximum gradient strengths ($G_{max}$) and 450 T/m/s slew rates which will increase SNR, since diffusion SNR $\alpha$ $e^{-TE/T2}$, where TE is the echo time and T2 is the spin relaxation time. Further, use of interleaved glass-fiber mats and ceramic components can reduce gradient mechanical (breathing, banana) resonances and attenuate noise by 10-20 dBA.

In general, early MR reception of the exponentially decaying MR signals will increase MRI SNR. For the operating frequency dependent human tissue ($\downarrow$T1, $\downarrow$T2) and 0.5T MR parameters explained above, the MR signal strength will increase 27% and 61% for MR receptions accelerated by 25 ms (e.g., from 35 to 10 ms) and 50 ms (e.g. from 60 to 10 ms), respectively. Faster encoding with the strong gradients will help achieve high MRI SNR with early MR signal reception. Very high $B1^+$ ($B_1$ transmit) can be attempted with a continuous or contiguously stacked RF pulses owing to the low field strength, allowing acquisition of higher flip angle 3D volumetric MRI scans with high SNR but without exceeding SAR. Flip angle or nutation angle or tip angle, $\alpha$ is the amount of rotation the net magnetization experiences during application of a RF pulse. Since the flip angle is proportional to B1 times the RF pulse-width, the net magnetization M depends on the B1 and RF pulse-width. Larger flip angles lead to larger MR signals, so long as it is not saturated (e.g., when TR>3T1), such is the case at 0.5T for most MR sequences.

In accordance with an aspect of the invention, B1 (flip angle) is increased while T1 (and therefore TR) is reduced. Increased flip angles result in increased signal based on MR physics, which leads to longer time for signal saturation, i.e. the signal and signal averaging are increased. Faster encoding then is used to maximize signal acquisition in the exponentially decaying MR signal. T2 is increased, which leads to longer TE (echo), multiple echo signals and higher imaging resolution. This is all possible at a $\frac{1}{3}^{rd}$ magnet field strength, thereby providing a signal obtainable from a 3× magnet field strength system.

Accordingly, with early acquisition (TE nearly zero, or zero) of exponentially decaying MR signals, more signal strength is acquired, which increases SNR. Longer T2 allows longer TE and the use of multiple imaging echoes. Prolonged signal acquisition also helps imaging signal and resolution.

Note at higher field strengths, T1 increases and T2 decreases, which works in quite the opposite manner compared to low field strength. At high field strengths, there may be RF-based SAR issues. At low field strength, i.e. at $\frac{1}{3}^{rd}$ field strength, the RF expended will be $\frac{1}{9}^{th}$, thus there will be no SAR issues and there will be very little or no chemical artifacts issues and/or signal saturation issues seen routinely at higher field strengths. At the lower field strength, the human tissue related MR parameters favor imaging without the SAR, safety and imaging constraints explained herein. At much lower field strengths, the signal drops off significantly, and is difficult to recuperate. The mid-field strength chosen herein is ideal for optimum SNR w/o experiencing safety issues commonly seen at higher field strengths. The concept exploits the field strength benefits and enhanced SNR without requiring higher field strengths. DWI comparative performance at 1.5T and with the inventive 0.5T MRI systems using identical imaging parameters of 24 cm FOV, b=1,000, spin-echo EPI imaging sequence, 200 KHz bandwidth readout, are discussed. For the inventive 0.5T MR system with a MR signal strength $S_0$=1, white matter T1 of 550 ms, min. TR of 70 ms, white matter T2 of 105 ms, TE of 53 ms and using the equation SNR=$S_0 \times e^{-TE/T2}/\sqrt{(\text{min. TR})}$, will result in a MRI SNR of 2.28. Whereas for a conventional clinical 1.5T MRI with a $S_0$=3 (based on three times the field strength of 0.5T), white matter T1 of 800 ms, min. TR of 136 ms, white matter T2 of 80 ms and TE of 97 ms will result in a MRI SNR of 2.42. As seen, the $SNR_{0.5T}$ (preferred scanner) is very close (within 5-6%) to the conventional MRI $SNR_{1.5T}$, at one-third the field strength. This deficit can be alleviated with an improved RF coil with 5-10% SNR increase, which is achievable. The above SNR can be further enhanced with an advanced RF coil with 40% SNR improvement. With such an improvement, the resultant $SNR_{0.5T}$ of the inventive scanner will be 1.32 times the $SNR_{1.5T}$. That is with an improved RF coil, the MRI SNR of the inventive scanner can match the SNR attainable on a conventional 2 T MRI scanner.

With respect to DWI and echo-planar imaging (EPI), faster gradients will relate to shorter TE and increased signal since the MRI signal is exponentially decaying with time. Faster gradients in a low field scanner will also relate to shorter TR, which in turn will lead to signal averaging thereby increasing MRI SNR, as described above. Longer T2 relaxation will lead to increased signal acquisition window, whereas three times lower field strength will drastically reduce image distortion due to non-linear $B_0$ and $B_1$ (RF wavelength) related artifacts commonly experienced at high field and UHF strengths. With respect to T2/FLAIR imaging sequence, very high RF B1 in the narrow pulse-width, wide bandwidth pulses will result in shorter echo trains and shorter TRs, which will increase SNR as mentioned above. In addition, shorter tissue T1 will result in full signal recovery (in 3T1 times) and lead to increased averaging also increasing MRI SNR. With no practical RF limit at the mid field strength, very short RF pulses can be attempted without exceeding FDA SAR guidelines. With respect to T1 weighted imaging (FLAIR, GRE etc.), shorter tissue T1 will lead to increased signal. High gradient and RF performances will lead to shorter echo trains. With respect to steady-state-free-precession (SSFP) sequences, faster gradients will result in efficient encoding and place off-resonance bands at higher ppm offsets, which will result in longer TR, which in turn will result in higher SNR using lower readout bandwidths (SNR $\alpha$ $\sqrt{BW}$).

Figure 9:
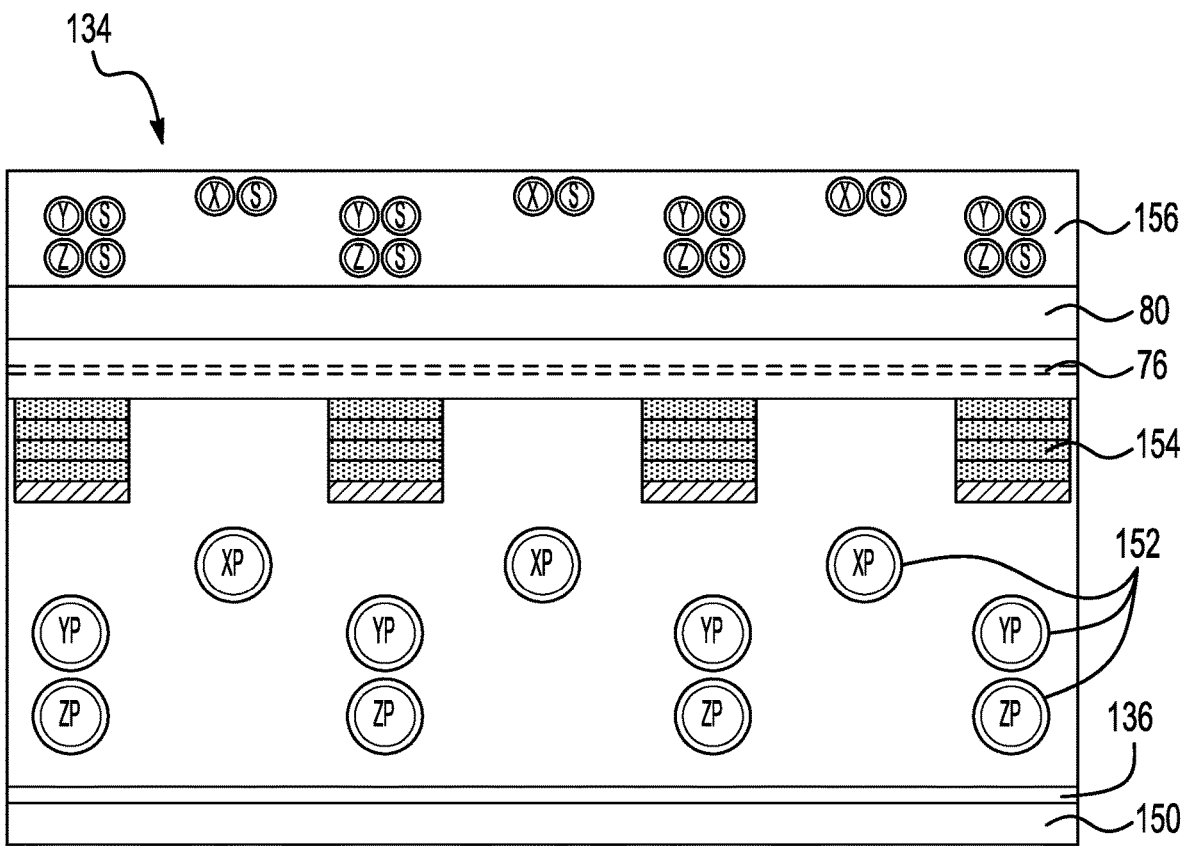
FIG. 9 is a simple schematic diagram showing a partial cross-sectional view of a connectome gradient assembly in accordance with the invention.

With reference to FIG. 9, a cross-section of a fiberglass potted connectome head gradient (cHG) 134 is shown (est. OD 59 cm, ID 42 cm). The use of advanced fiberglass manufacturing techniques enables operation without overheating or torque-induced stress at noise levels<110 dBA. The connectome head gradient 134 includes a noise attenuating layer 150, 5 μm thick RF mesh (RF shield 136), X-Y-Z tubular primary windings 152 with water cooling, high-order resistive shims 154, room-temperature shim tray 76 with 32 steel pieces, mechanical stiffener 80 and secondary windings 156 with water cooling are shown. With respect to cooling, a compact 10-Ton (35 kWh) commercial medical air chiller is adequate to cool the magnet (6 kW) and to support maximum gradient (18 kW) performance (101 mT/m Gmax, 450 T/m/s slew rate). Optionally, a reservoir of water-glycol mixture can be replaced with a ten-fold thermal conductivity improved (0.05 W/m·K) heat transfer fluid (FC-70, 3M) for efficient operation.

A torque-balanced asymmetric design will eliminate stress due to Lorentz's force and torque on the fiberglass potting. Use of glass-fiber mats, glue and resin with proprietary manufacturing techniques will reduce gradient structure mechanical (breathing and 'banana') resonances, which can otherwise weaken the structure. Mechanical resonance Eigen modes can be verified on the resistance versus frequency curve for the gradient proposed herein. Novel use of copper tubes as opposed to sheets will enhance gradient efficiency to achieve high maximum strength (Gmax) and fast slew rates, which is ideal for use with diffusion MR Sequences. Use of proprietary ceramic components to attenuate gradient induced noise by 10-20 dBA can be used.

Preferably, 150 mT/m maximum strength and 800 T/m/s maximum slew rate can be achieved with good linearity (>90%) over a 25 cm FOV sufficient to image the human brain. It is possible that the IEC dB/dt whole-body limit of 80 $TS^{-1}$ may be exceeded, but only in the brain, which has no published stimulation thresholds or dB/dt limits at present. With the preferred embodiment, overall magnet-gradient assembly weight of approximately 1,500 Kgs will be distributed over a 6'×8' floor area in the 14'×8' ambulance second section 66 (rear cab). The strong connectome head gradients can be liquid cooled. The SC magnet operation can be supported with a small compressor and dedicated water cooler. The rest of the MR electronics can be cooled with air circulation.

At mid to low field strengths, dielectric resonances in the human head are not much of a problem (unlike in the high and ultra-high field strengths (3T, 7T, etc.)). Non-linear phase currents are not expected and therefore the transmit RF coil 138 can be driven in quadrature using a single RF channel. Should better RF uniformity be desired, two transmit channels necessary to drive the individual birdcage linear modes may be utilized. Regardless, expended RF to conduct the brain MR experiment is estimated to be roughly $\frac{1}{10}^{th}$ of that used by the whole-body coil on the clinical 1.5T clinical MRI scanner. The low magnetic field and the low RF will be ideal for use on patients with metal fragments or the ones with cardiac pacemakers and/or defibrillators. The latter is practicable, since the torso will be outside the scanner and outside the FOV of the body RF transmit coil. With the transmit RF coil 138, $B_1$ fields of equal to or greater than 50 μT are possible, which will permit high bandwidth RF pulses with a 1 kW RF amplifier. In all cases, the RF power deposition will be below the FDA limit of 3.2 W/Kg for SAR over the human brain.

Multichannel receiver head array RF coils can be utilized to maximize MRI SNR but without touching the subject. With the fixed RF transmit coil 138 and RF coil localization, MR quantitation is also possible. With the fast-switching (~1 μs) receiver array RF coils 140, parallel imaging, multi-band MRI and compressed imaging are possible, all of which are intended to image the bone, muscle, nerve, tissue and blood vessels rapidly, with very short or zero TE sequences.

For a receiver chain with 3 gain stages, the total noise factor can be found with Friis' Formula:

$$\text{Friis' Formula} := N1 + \frac{N2-1}{G1} + \frac{N3-1}{G1G2},$$

where N1-N3 and G1-G3 are noise figures and gains for the three individual stages. The first amplifier in a chain (preamplifier in the coil) usually has the most significant effect on the total noise figure because the noise figures of the following stages are reduced by stage gains. Consequently, the first amplifier usually has a low noise figure, and the noise figure requirements of subsequent stages are usually more relaxed. It has been found that should the first RF receiver gain be roughly a third or more of the entire receiver gain, noise figure of the entire chain and therefore overall SNR can be preserved.

SNR can be increased by increasing the signal or reducing noise. An MR signal obtainable from an object is fixed for a given RF coil design, imaging sequence and field strength. To further maximize SNR performance the circuitry noises should be reduced to a minimum and preferably almost to zero, although they cannot be eliminated entirely. The use of high permittivity material (HPM), conductive particles (σ≤15 mS/cm) placed within or close to the RF coil and/or super cooling the RF coils to increase signal and reduce overall noise can be used.

Receive signals are digitized either on the coil or very near the magnet prior to signal combination preferably at the NMR frequency. Analog, digital, optical or other means may be employed in the receiver chain. Processing and post-processing can be hosted on the imaging console or on separate consoles. It is worth noting scanner electronics can be placed in a 4'×4' area, with the imaging operator console screen either fastened to the main magnet or inside the emergency ambulance section. Thus, the space required for the MRI install will be well within the 8' wide×14' long emergency ambulance section (rear cab).

Figure 10:
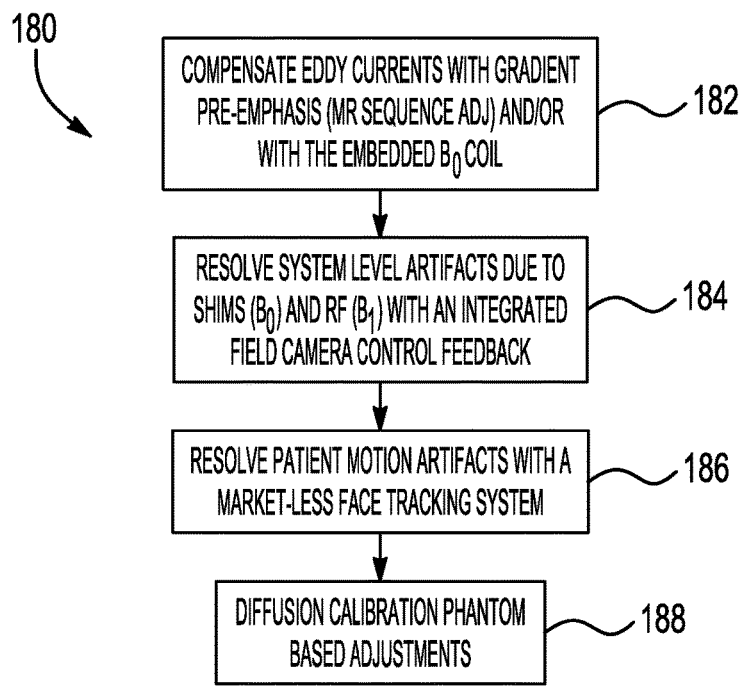
FIG. 10 is a slow chart illustrating dynamic mechanisms for resolving system level artifacts and patient motions induced artifacts in accordance with the invention.

The flow-chart 180 of FIG. 10 depicts inventive ways to improve MR image quality. More particularly, compensation can be provided for eddy currents with gradient pre-emphasis and/or with the embedded BC coil. Further, corrections can be made to counter system level perturbations caused by shims and gradients (block 184), and patient motion corrections can be made using a marker-less tracking system and prospective algorithms (block 186). Additionally, system calibration can be performed on a custom anisotropic diffusion MRI (AdMRI) phantom for proper verification of sequences and validation of microstructural measurements (block 188).

As shown at block 182, system level eddy currents can be counteracted with gradient pre-emphasis intended to compensate linear $B_0$ terms and dynamically use the embedded $B_0$ coil within gradients to offset slice shifts. High-order shims, sequence adjustments to minimize field perturbations, and other means to nullify phase effects on the gradient echo images will help to minimize system induced artifacts.

As shown at block 184, to offset MR system level image artifacts due to $B_0$ (shim) and $B_1$ (RF) phase errors, employment of an integrated field monitoring system camera with feedback will assist to adjust every MR sequence dynamically or prospectively. As shown at block 186, the dynamic field camera inside the MRI system can deliver the requisite input to remove image phase errors and offer real-time feedback for field stabilization. Likewise, integration of a marker-less optical face camera system with dynamic retrospective motion correction algorithms can offset patient motion and deliver artifact-free diagnostic quality images. As shown at block 188, for MR standardization, quality assurance and quantification, MRI calibration can be made on a high-fidelity anisotropic diffusion MRI phantom, since it provides measurement of "ideal axons" in the order of 10-50 µm thickness with known angular rotations that are mathematically tractable and not possible in tissue validation studies. With DWI it is possible to identify areas of focal injury and abnormal brain development. In order to clearly differentiate between the isotropic and anisotropic water molecule motion, operators need a standard value for diffusion states, which also serves as a scientific reason for integrating the diffusion phantom with the MRI system. The custom phantom can include several 10-25 ml vials of 10-50% conc. of NIST certified polyvinylpyrrolidone dissolved in water to serve as standards for different diffusion rates in the human brain. The diffusion calibration phantom can include different known Taxon configurations (6-44 micron ID), track-crossings (30-90°) and densities (0-100%) to aid MRI measurements. Phantom measurements from the previous diffusion calibration study can be used to adjust and to ensure proper diffusion values, angles and thicknesses are deduced.

Other ambulance, power generation, magnet, gradient, RF, transmit-receive, sequence development, protocols development, image acquisition, reconstruction, post-processing and display designs and arrangements are possible.

Narrow and broad band filtering schemes over the NMR spectrum, shielded coaxial cables, better grounding, etc. and double faults are included to reduce EMI/EMC radiation (per IEC 60601-1-2), eliminate undesired harmonics, minimize risks of high voltage exposure while maintaining leakage currents below the required IEC guidelines for medical equipment for safe operation (IEC 60601-1). All of the MRI compatible equipment and accessory (ventilator, monitor, infusion pump, IV bag, oxygen/air tanks, pressure reducers, flow tubes, etc.) are held on to the accessible MRI emergency ambulance and safe to enter the ambulance emergency section, whereas non-magnetic and MR unsafe accessory are removed from the ambulance emergency section. In the best interest of saving the gases remaining in the MR conditional tanks, quick connect-disconnects can be provided to switch over between the gas tanks and/or the hospital supply lines in a matter of seconds.

Proximity to the subject enhances SNR owing to higher filling factors. See U.S. Pat. No. 6,992,486 to Srinivasan, which is incorporated by referenced in its entirety, for an example of a close-fitting coil intended to improve SNR on infants. A similar approach can be taken here. Parallel imaging compatible array coils further enhance image quality. Parallel transmit capability can lead to reduction of peak and average SARs over infants. Other coil combinations, such as a knee coil, head only coil, wrist coil, abdomen coil, etc. can be realized for use with the MRI scanner and an isolette. The present invention is not just limited to EPR, ESR or NMR techniques. Leaving the magnet at lower field strength or turning it OFF after use may be beneficial to enhance safety or to allow cleaning personnel or to conserve power.

Modifications to the accessible system, emergency ambulance MRI zones (III, IV), vehicle, suspension system, magnet, magnetic shielding means, gradients, shims, RF shield, MRI, transmit chain originating from the transmit body coil, receive chain originating from the local imaging devices, direct or indirect warming systems, support equipment and accessory are plausible by someone skilled in the art after reading this application.

A preferred example of a 0.5T inventive scanner comparable in performance to a conventional 1.5T MRI scanner is described. It should be understood that other examples can be readily apparent to someone skilled in the art, such as a 1.5T inventive scanner exceeding conventional 3T MRI performance; or a 3T head scanner comparable in performance to a 7T conventional MRI scanner; or a 7T scanner exceeding the conventional 10.5T MRI are now practicable. It should also be readily apparent to one skilled in the art to install the inventive MRI to satisfy diverse mobile and/or stationary applications.

Further, the use of efficient batteries, generator(s), alternate power and/or uninterrupted power supplies assist to support the MRI magnet and electronics suitable for imaging for short periods. In this regard, a Tesla X, Panasonic 100 kWh (403.2V, 248A), deep-cycle lithium-ion battery can provide up to four hours of mobile MRI operation at 24 kWh (400V, 60A) is achievable. Per the AHA/ASA recommendations, imaging must include DWI functionality and shorten time to clinical diagnosis followed by immediate clinical intervention and treatment for improving outcome in stroke patients.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A mobile magnetic resonance imaging (MRI) system, comprising:
   a damper system;
   a support structure attached to the damper system;
   a mid-field super-conducting magnet attached to the support structure, the magnet including:
      a bore and an active shield arranged relative to the magnet;
      a passive shield arranged relative to the magnet, the passive shield including
         a first flange arranged adjacent to a first side of the magnet bore;
         a second flange arranged adjacent to a second side of the magnet bore,
      wherein the first flange and the second flange are electrically connected to each other, and
         wherein the passive shield is operative to capture flux extending out from the magnet bore and return the flux to the magnet;
   an asymmetric head gradient assembly for generating magnetic gradient field in the mid-field super-conducting magnet, the magnetic gradient field being between 100-150 mT/m or having a slew rate between 400-800 T/m/s;
   a transmit coil;
   a receiver coil; and
   a controller operatively coupled to the transmit coil and the receive coil, the controller configured to produce an image based on data obtained from the receive coil.

2. The mobile MRI system according to claim 1, wherein the damper system includes:
   a plurality of vibration dampers, and
   a storage bank coupled to the plurality of vibration dampers, the storage bank including a computer-controlled gyroscope-feedback circuit and dynamic liquid viscosity altering current control to control at least one of shock absorption and vibration damping.

3. The mobile MRI system according to claim 1, further comprising an emergency vehicle comprising a frame to which wheels of the vehicle are attached, wherein the support structure is attached to the frame via the damper system.

4. The mobile MRI system according to claim 3, wherein the damper system comprises a shock absorber, a pneumatic spring, and a liquid bank with dynamic fluid viscosity control.

5. The mobile MRI system according to claim 1, wherein the gradient assembly comprises a split configuration having a first coil portion and a second coil portion, the first and second coil portions electrically connected in parallel with each other.

6. The mobile MRI system according claim 1, wherein the passive shield comprises a plurality of circular tubes arranged around an outer circumference of the magnet, the plurality of circular tubes connecting the first flange to the second flange.

7. The mobile MRI system according to claim 1, wherein the passive shield comprises a plurality of rectangular segments arranged around an outer circumference of the magnet, the plurality of rectangular segments connecting the first flange to the second flange.

8. The mobile MRI system according to claim 1, wherein the passive shield comprises a metallic sheet arranged around an outer circumference of the magnet, the metallic sheet connecting the first flange to the second flange.

9. The mobile MRI system according to claim 1, wherein the magnet comprise a cryogen-free cooler operative to cool the magnet.

10. The mobile MRI system according to claim 1, wherein the mid-field superconducting magnet comprises niobium-titanium-copper wire reinforced with a stainless-steel alloy.

11. The mobile MRI system according to claim 1, further comprising a restraining device coupled to the magnet to secure the magnet to the support structure, wherein the restraining device comprises multi-layer magnetic shielding.

12. The mobile MRI system according to claim 1, wherein the head gradient assembly includes a noise attenuating layer, an RF shield, and three-axis windings.

13. The mobile MRI system according to claim 1, wherein the patient table is movable relative to the magnet.

* * * * *